(12) United States Patent
Olszowy

(10) Patent No.: US 12,203,914 B2
(45) Date of Patent: Jan. 21, 2025

(54) VIRAL CLEARANCE EVALUATION FOR BIOLOGICAL MEDICAL PRODUCT PREPARATION PROCESSES

(71) Applicant: Sartorius BioAnalytical Instruments, Inc., Bohemia, NY (US)

(72) Inventor: Michael W. Olszowy, Erie, CO (US)

(73) Assignee: Sartorius BioAnalytical Instruments, Inc., Bohemia, NY (US)

( * ) Notice: Subject to any disclaimer, the term of this patent is extended or adjusted under 35 U.S.C. 154(b) by 715 days.

(21) Appl. No.: 17/096,681

(22) Filed: Nov. 12, 2020

(65) Prior Publication Data

US 2022/0146485 A1   May 12, 2022

(51) Int. Cl.
C12Q 1/04          (2006.01)
G01N 21/64         (2006.01)
G01N 33/15         (2006.01)

(52) U.S. Cl.
CPC ............ *G01N 33/15* (2013.01); *C12Q 1/04* (2013.01); *G01N 21/6428* (2013.01); *G01N 2021/6439* (2013.01)

(58) Field of Classification Search
None
See application file for complete search history.

(56) References Cited

U.S. PATENT DOCUMENTS

| | | | |
|---|---|---|---|
| 9,632,087 | B2 | 4/2017 | Cetlin et al. |
| 10,309,963 | B2 | 6/2019 | Cetlin et al. |
| 2012/0070818 | A1 | 3/2012 | Rowlen et al. |
| 2015/0232911 | A1 | 8/2015 | Rowlen et al. |
| 2018/0052163 | A1 | 2/2018 | Artinger et al. |
| 2021/0239581 | A1 | 8/2021 | Montange et al. |
| 2023/0103302 | A1* | 4/2023 | Kayukawa ........... C12Q 1/6851 435/5 |

FOREIGN PATENT DOCUMENTS

| | | |
|---|---|---|
| EP | 2377927 B1 | 5/2019 |
| WO | 2013138159 A1 | 9/2013 |
| WO | 2018045278 A1 | 3/2018 |
| WO | 2018075716 A1 | 4/2018 |
| WO | 2019011900 A1 | 1/2019 |
| WO | 2020028639 A1 | 2/2020 |
| WO | 2020197644 A1 | 10/2020 |

OTHER PUBLICATIONS

AAT Bioquest, Safety Data Sheet, Revision Date Mar. 27, 2023. (Year: 2023).*
Leisi et al., Journal of Membrane Science, Mar. 5, 2020, 603:118012, pp. 1-14. (Year: 2020).*
Strauss et al., Biotechnology and Bioengineering, 2009, 104(2):371-380. (Year: 2009).*
Rockey et al., Current Opinion in Biotechnology 2019, 57:42-49. (Year: 2019).*
Gitis et al., Fluorescent dye labeled bacteriophages—a new tracer for the investigation of viral transport in porous media: 2. Studies of deep-bed filtration, Water Research, vol. 36, (2002), pp. 4235-4242.
Gitis et al., Fluorescent dye labeled bacteriophages—a new tracer for the investigation of viral transport in porous media: 1. Introduction and characterization, Water Research, vol. 36, (2002), pp. 4227-4234.
A Guide to Planning Your Viral or TSE Clearance Study, BioReliance by SAFC, www.bioreliance.com, (2012), 18 pages.
Easy molecular bonding. Crosslinking technology. Reactivity chemistries. applications and structure references. Crosslinking Technical Handbook, Thermo Scientific (part of Thermo Fisher Scientific), (2012), 56 pages.
Hermanson, Greg. Amine-Reactive Corsslinker Chemistry, Thermo Fisher Scientific, Bioconjugate Techniques, 3rd Edition, (2013); 8 pages.
Amine-Reactive Crosslinker Chemistry, Thermo Fischer Scientific, undated, 7 pages. Retrieved Mar. 29, 2020, from https://www.thermofisher.com/us/en/home/life-science/protein-biology/protein-biology-learning-center/protein-biology-resource-library/pierce-protein-methods/amine-reactive-crosslinker-chemistry.html.
Banks et al, Comparison of Three Common Amine Reactive Fluorescent Probes Used for Conjugation to Biomolecules by Capillary Zone Electrophoresis, Biconjugate Chem., vol. 6, (1995), pp. 447-458.
Leisi, Remo et al, "Determination of parvovirus retention profiles in virus filter membranes using laser scanning microscopy", Journal of Membrane Science, 603 (2020) 118012, Mar. 5, 2020, Elsevier BV, NL, 21 pages, including 7 pages of Supplementary Material.
Min Zhang et al, "Quality by design approach for viral clearance by protein a chromatography", Biotechnolgy and Bioengineering, vol. 111, No. 1, 2014, Epub Aug. 16, 2013, John Wiley, Hoboken, USA, pp. 95-103.
WHO Technical Report, Series No. 924, 2004, Annex 4, "Guidelines on viral inactivation and removal procedures intended to assure the viral safety of human blood plasma products", Jan. 1, 2004, World Health Organization, pp. 150-224.
Valera, Christine R et al, "Application of Multivirus Spike Approach for Viral Clearance Evaluation", Biotechnology and Bioengineering, vol. 84, No. 6, Dec. 20, 2003, Wiley Periodicals, Inc., pp. 714-722, published online Oct. 21, 2003 at www.intersicence.wiley.com.

* cited by examiner

*Primary Examiner* — Nicole Kinsey White
(74) *Attorney, Agent, or Firm* — Holzer Patel Drennan

(57) ABSTRACT

Fluorescent viral particles, including viral particles and a fluorescent dye conjugated to the viral particles, are used for viral contaminant removal testing as part of viral clearance evaluation for biological medical product preparation processes. The conjugated fluorescent dye adds only marginally to viral particle size, but provides versatility both for rapid screening of alternative viral removal approaches during process development and for final process validation, as the fluorescent viral particles have fluorescent activity throughout the viral clearance evaluation process, permitting rapid and consistent quantification of initial test solutions, resulting purified solutions, and intermediate solutions of interest at any point during processing under evaluation.

23 Claims, 12 Drawing Sheets

VIRAL CLEARANCE EVALUATION FOR BIOLOGICAL MEDICAL PRODUCT PREPARATION PROCESSES

FIELD

The invention relates to viral clearance evaluation using fluorescent viral particles as test contaminants for challenge of purification processing of biological medical product preparation processes, and including related methods, products and kits.

BACKGROUND

Biological medical products, also referred to as biopharmaceutical products or biologics, include biological material obtained from biological sources, for example by extraction from tissue or biological fluids or generated in a cell culture or fermentation operation. Some examples of biological medical products include hormones, interferons, monoclonal antibodies and recombinant DNA-derived products. Biological medical products are, however, susceptible to contamination during manufacturing by viruses not desired for inclusion in the final biological medical product, and in some cases such viral contaminants can pose significant health risks to patients. Viral contaminants may include endogenous viruses associated with a biological production operation or adventitious viruses that invade and reproduce in the biological production operation. Accordingly, biological medical product preparation processes must be designed to ensure effective clearance of such viral contaminants, whether or not the preparation process ever becomes contaminated with such viral contaminants, to ensure the safety of resulting biological medical products. Regulatory approval of biological medical product preparation processes often requires demonstration of the effectiveness of the process for viral contaminant clearance.

Clearance of viral contaminants may occur by removal and/or inactivation of viral contaminants. Viral clearance processing in a biological medical product preparation process may include one or more viral contaminant inactivation techniques and/or one or more viral contaminant removal techniques. Some examples of inactivation techniques include chemical treatment, (e.g., by solvents or detergents), pH treatment, UV light treatment and heat treatment. Different inactivation methods have different degrees of effectiveness depending upon the particular viral contaminant. A limitation on the use of chemical and heat treatments often associated with inactivation methods is that such treatments may be detrimental to the biological medical product of interest.

Viral contaminant removal may be effected by one or more techniques designed to selectively separate particles of a viral contaminant from the biologic material of interest, which may include for example processing to remove a viral contaminant from a process solution containing the biologic material of interest and/or processing to remove the biologic material of interest from a process solution that might also contain viral contaminants. Some examples of virus removal techniques include affinity separation techniques (e.g., affinity chromatography), filtration (e.g., nanofiltration) and centrifugation.

Viral clearance studies, also referred to as virus spiking studies or viral spiking studies, are evaluation studies undertaken to demonstrate effectiveness of biological medical product preparation processes for efficacy to ensure clearance of viral contaminants by inactivation, removal or both. Such viral clearance studies may involve preparing one or more evaluation solutions including the biological material of interest and an added test contaminant, typically in the form of virus particles (virions). A test contaminant may be representative of an actual anticipated viral contaminant (e.g., the same virus as a virus of actual concern) or may be a surrogate contaminant (e.g., a virus other than a virus of actual concern). More recently, test contaminants have been proposed that have viral attributes but that are non-infectious and non-replicating particles, such as virus-like particles, to reduce some of the safety concerns around the use of virions.

Demonstration of viral contaminant clearance through removal may involve spiking of test solutions with the test contaminant and subjecting the test solutions to one or more removal techniques under simulated process conditions. Successful testing may require demonstration of a high level of removal of the test contaminant as indicated by multiple logarithmic reductions (also referred to as $\log_{10}$ reduction or simply log reduction) in the amount of the test contaminant between the initial spiked test solution and a purified solution following purification processing that is the subject of the evaluation. The log reduction demonstrated during evaluation is sometimes referred to as the Log Reduction Factor (LRF) or Log Reduction Value (LRV). For example, some viral clearance evaluations may require demonstration of at least a four log reduction (LRF or LRV of 4 or greater) in the amount of the test contaminant between the initial test solution and such a purified solution. The evaluation of removal efficiency of viral contaminant particles will typically involve analytical quantification of a residual amount of the viral contaminant particles in the purified solution and comparison of that residual amount with the initial load of the viral contaminant particles in the initial test solution. Common analytical quantification techniques include infectivity assays, such as tissue culture infective dose assay ($TCID_{50}$ assay) or plaque forming unit assay (PFU assay), which are time consuming and expensive. Samples may also be evaluated using quantitative polymerase chain reaction (qPCR) analysis or enzyme-linked immunosorbent assays (ELISA).

Viral clearance studies tend to be very expensive and logistically complicated and time consuming to plan and perform, and the consequences of failure to demonstrate a required effectiveness for viral clearance can be serious. Failure of a viral clearance study may require redesign of the biological medical preparation process, performance of a new viral clearance study on the redesigned process, and delay of regulatory approval.

SUMMARY

Fluorescent viral particles, including viral particles and a fluorescent dye conjugated to the viral particles, have been found to be advantageous for use in viral contaminant removal testing as part of viral clearance evaluation for biological medical product preparation processes. The fluorescent viral particles may be employed as test contaminants to challenge proposed purification processing under evaluation for viral contaminant removal in a biological medical product preparation process. The presence of the conjugated fluorescent dye adds only marginally to viral particle size, but provides versatility both for rapid screening of alternative viral removal approaches during process development and for final process validation, all using a single, convenient viral clearance evaluation platform. The fluorescent viral particles have fluorescent activity throughout the viral clearance evaluation process, permitting rapid and consistent quantification of initial test solutions, resulting purified solutions, and intermediate solutions of interest at any point during processing under evaluation. Quantification may conveniently be performed using the fluorescent properties of the fluorescent viral particles, and without the added time and complexity otherwise required to fluorescently label viral particles at the time of quantification analysis. Avoiding fluorescent labelling at the time of quantification analysis permits rapid and convenient quantification analysis of samples for evaluation of viral contaminant removal, and advantageously without the chemical changes to samples that would otherwise result from fluorescent labeling at the time of quantification analysis and inaccuracies in quantification results that could be introduced by such chemical changes. The method also advantageously permits the fluorescent viral particles to be provided as a pre-prepared standard reagent product for versatile and convenient use for testing across a wide variety of different virus purification techniques and across a wide variety of model virus types, both for tests using virus particles (virions) and for tests using non-infectious, non-replicating viral particles such as virus-like particles.

A first aspect of this disclosure concerns methods using fluorescent viral particles for viral clearance evaluation for a biological medical product preparation process. In some embodiments, a method of this first aspect may comprise:

subjecting an evaluation solution to purification processing to prepare a treated solution, wherein the evaluation solution comprises a biological medical product and fluorescent viral particles, and wherein the purification processing comprises a viral removal technique for separation of a viral contaminant from the biological medical product; and determining a degree of removal of the fluorescent viral particles between the evaluation solution and the treated solution; and wherein the fluorescent viral particles comprise viral particles and a fluorescent dye conjugated to the viral particles.

A second aspect of this disclosure concerns viral standard products including fluorescent viral particles, optionally for use in a method of the first aspect. In some embodiments, a viral standard product of this second aspect may comprise:

a viral standard solution comprising an analytically quantified number concentration of fluorescent viral particles dispersed in a standard liquid medium, the fluorescent viral particles comprising viral particles and a fluorescent dye conjugated to the viral particles; and a container, preferably a sealed container, containing the viral standard solution, the container comprising viral standard indicia, the viral standard indicia including identity of the viral particles and the analytically quantified number concentration, and the viral standard indicia preferably being exteriorly observable.

A third aspect of this disclosure concerns kits including fluorescent viral particles for viral clearance evaluation for a biological medical product preparation process, optionally in a method of the first aspect. In some embodiments, a kit of this third aspect may comprise:

a viral standard product, optionally of the second aspect, the viral standard product comprising a container, preferably a sealed container, containing a viral standard solution for use to prepare evaluation solutions comprising a biological medical product for viral clearance evaluation; and at least one virus removal device for testing removal of the fluorescent viral particles during purification processing of a said evaluation solution to prepare a treated solution for the viral clearance evaluation; and wherein, the viral standard solution comprises an analytically quantified number concentration of fluorescent viral particles dispersed in a standard liquid medium, the fluorescent viral particles comprising viral particles and a fluorescent dye conjugated to the viral particles.

A fourth aspect of this disclosure concerns methods for making a viral standard product, optionally of the second aspect, including fluorescent viral particles. In some embodiments, a method of this fourth aspect may comprise:

harvesting viral particles from a viral particle production operation, as harvested the viral particles being in a harvest solution comprising biological contaminants;

following the harvesting, purification processing of the viral particles to prepare a purified process solution containing the viral particles;

fluorescent labeling the viral particles in the purified process solution to prepare a labeled process solution comprising fluorescent viral particles, the fluorescent labeling comprising conjugating a fluorescent dye to the viral particles; and after the fluorescent labeling, preparing a batch of viral standard solution comprising a batch of the fluorescent viral particles dispersed in a standard liquid medium;

analytically quantifying a number concentration of the fluorescent viral particles in the batch of the viral standard solution; and disposing a volume of the batch of the viral standard solution in a container, preferably a sealed container, wherein the container comprises thereon viral standard indicia including identity of the viral particles and the analytically quantified number concentration, and preferably the viral standard indicia is exteriorly observable.

A number of other feature refinements and additional features are applicable to each of these and other aspects of this disclosure. These feature refinements and additional features may be used individually or in any combination within the subject matter of this aspect or any other aspect of this disclosure. As such, each of the following features may, but are not required to be, used with any other feature or a combination of features of this aspect or any other aspect of this disclosure. The viral standard solution of a product of the second aspect or provided in a kit of the third aspect may be used to prepare the evaluation solution for the method of the first aspect. Such a viral standard solution may be made using a method of the fourth aspect. A product of the second aspect and/or a kit of the third aspect may be used in performance of a method of the first aspect.

Numerous additional feature refinements and additional features applicable to these and other aspects of this disclosure are further disclosed in the drawing, the description provided below and the appended claims.

BRIEF DESCRIPTION OF THE DRAWINGS

Elements shown in the figures in broken lines are optional features of the illustrated example embodiments, unless otherwise stated. The same reference numerals are used in the different figures to identify the same features.

DETAILED DESCRIPTION

FIGS. 1-7 show process diagrams for various example embodiments related to the method of a first aspect of this disclosure.

Figure 1:
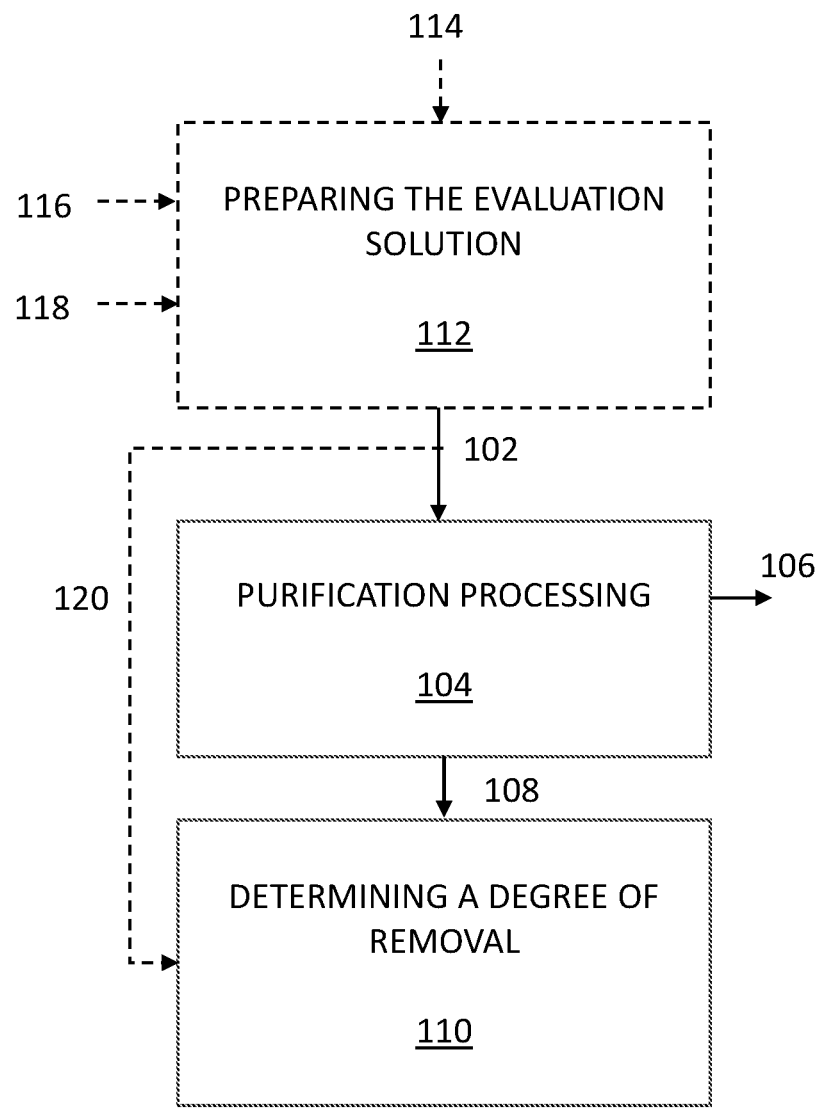
FIG. 1 is a process diagram illustrating processing of some example embodiments of a method of viral clearance evaluation.

FIG. 1 illustrates general processing in which an evaluation solution 102, having a biological medical product and fluorescent viral particles, is subjected to purification processing 104, including at least one viral removal technique to prepare a viral contaminant waste effluent 106 and a treated solution 108. During the purification processing 104, biological medical product and the fluorescent viral particles in the evaluation solution 102 partition between the effluent 106 and the treated solution 108, such that in a typical processing situation the fluorescent viral particles preferentially partition into the effluent 106 and the biological medical product preferentially partitions into the treated solution 108, whereby the treated solution 108 is in a more purified state with respect to the biological medical product relative to the evaluation solution 102. As may be appreciated, the effluent 106 is shown as a single resulting stream, but may comprise a plurality of resulting streams, for example when the purification processing 104 includes a plurality of viral removal techniques that each generates a separate effluent stream.

After the purification processing 104, the treated solution 108 is subjected to processing 110 of determining a degree of removal of the fluorescent viral particles between the evaluation solution 102 and the treated solution 108 (e.g., LRF or LRV) indicating a level of effectiveness of the purification processing 104 for separation of the fluorescent viral particles from the biological medical product, and by extension an indication of a level of effectiveness of the purification processing 104 to separate viral contaminants (e.g., virions) from the biological material product during operation of a biological medical product preparation process.

Also as shown in FIG. 1, the illustrated processing example includes optional processing of preparing the evaluation solution 102. During the processing 112, a feed volume of a preliminary feed solution 114 is combined with a reagent volume of a viral standard solution 116 comprising the fluorescent viral particles dispersed in a standard liquid medium at a known analytically quantified number concentration. The respective volumes of the preliminary feed solution 114 and the viral standard solution 116 combined in the processing step 112 provide a desired evaluation concentration of the biological medical product in the evaluation solution 102 and a desired loading of the evaluation solution 102 with the fluorescent viral particles for the challenge of the purification processing 104. Also shown for the processing 112 is an optional provision of a reagent 118 for combining with the preliminary feed solution 114 and the viral standard solution 116 to provide any desired adjusted properties for the evaluation solution 102. An example of such a reagent 118 may be an acidic or basic solution to adjust pH of the evaluation solution 102 to a desired pH for the purification processing 104.

The example processing illustrated in FIG. 1 also includes an optional feature of providing a portion 120 of the evaluation solution 102 to the processing 110 to permit a small sample volume of the evaluation solution 102 to be subjected to an analytical technique to analytically quantify a feed concentration of the fluorescent viral particles in the evaluation solution 102, to provide an analytically determined starting amount of fluorescent viral particles in the evaluation solution 102 for comparison with a residual amount of the fluorescent viral particles in the treated solution 108 to determine the degree of removal of the fluorescent viral particles as a consequence of the purification processing 104. Alternatively, or additionally, the general processing illustrated in FIG. 1 could utilize the predetermined analytically quantified number concentration of the fluorescent viral particles reported for the viral standard solution 116 to determine a calculated starting amount of the fluorescent viral particles in the evaluation solution 102. In a contemplated processing alternative, such an analytically determined starting amount of fluorescent viral particles in the evaluation solution 102, determined by analysis of the portion 120 of the evaluation solution 102, may be compared to such a calculated starting amount of the fluorescent viral particles to evaluate for a possible degree of post-manufacture degradation (e.g., aggregate formation) of the viral standard solution 116 prior to utilization for viral clearance evaluation in the processing illustrated in FIG. 1. In such a processing alternative, it is preferred that the analytical quantification technique utilized to generate the analytically determined starting amount is comparable to, and more preferably is substantially the same as, the analytical quantification technique used to generate the analytically quantified number concentration of the fluorescent viral particles in the viral standard solution 116 (e.g., both being flow cytometry, and more preferably using the same or comparable model flow cytometer). In another contemplated processing alternative, the processing 110 may include determining a degree of removal of the fluorescent viral particles between the evaluation solution 102 and the treated solution 108 based on each of such an analytically determined starting amount and such a calculated starting amount for the fluorescent viral particles in the evaluation solution 102, to independently assess for each such starting amount a degree of removal of the fluorescent viral particles from the biological medical product during the purification processing 104.

For analytical quantification of fluorescent viral particles, whether in the evaluation solution 102 or the treated solution 108, or for determination of the analytically quantified concentration of the viral standard solution 116, a preferred analytical quantification technique is flow cytometry. One preferred flow cytometer for analytical quantification of fluorescent viral particles is the Virus Counter® 3100 flow cytometer (Sartorius Stedim Biotech). Flow cytometry evaluation may include preparing a dilution series including diluted samples at different dilution ratios and subjecting each of the samples of the dilution series to flow cytometry. The flow cytometry results for the dilution series may then be evaluated to determine titer (concentration) of the fluorescent viral particles in the undiluted sample. For example, flow cytometry concentration results for the different diluted samples may be plotted on a log-log scale and evaluated for plot linearity, as is common in flow cytometry evaluation using the Virus Counter® 3100 flow cytometer.

FIGS. 2-7 illustrate various example embodiments of more specific processing that may be included within the general processing context illustrated in FIG. 1.

Figure 2:
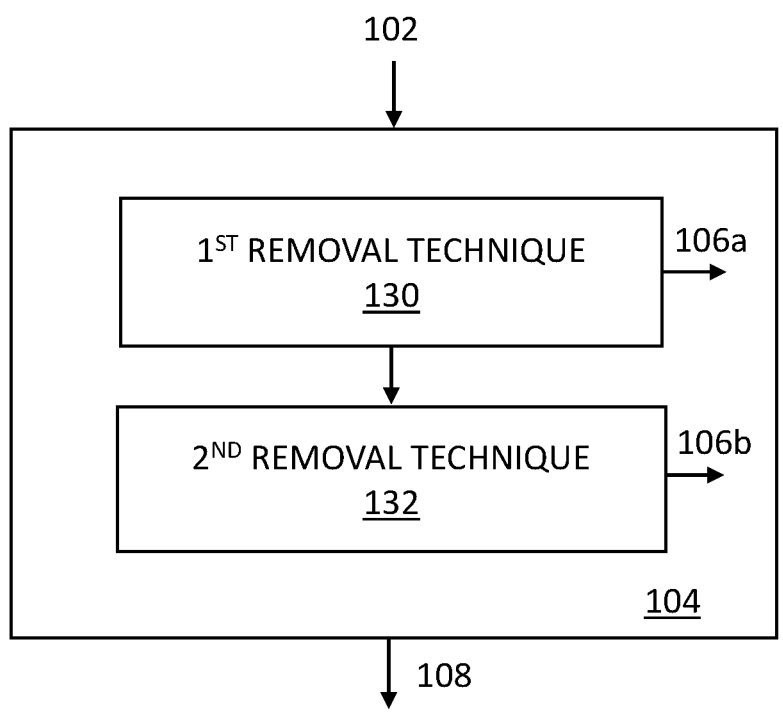
FIG. 2 is a process diagram illustrating some example embodiments of more specific processing within the general processing context of FIG. 1.

FIG. 2 illustrates an example of processing within the purification processing 104 of FIG. 1, in which the evaluation solution 102 is subjected to a plurality of different viral removal techniques arranged in series to prepare the treated solution 108. For illustration purposes, the purification processing 104 shown in FIG. 2 includes a first viral removal technique 130 in which a first portion of the fluorescent viral particles are separated from the biological material product and a second viral removal technique 132 in which a second portion of the fluorescent viral particles are separated from the biological material product. As may be appreciated, such processing as illustrated in FIG. 2 may include more than two different viral removal techniques arranged in series. In the processing illustrated in FIG. 2, the treated solution 108 has a reduced amount of the fluorescent viral particles representing a cumulative separation of the fluorescent viral particles from the biological medical product as a combined consequence of both the first viral removal technique 130 and the second viral removal technique 132 to prepare the treated solution 108. In the example processing shown in FIG. 2, a first viral contaminant effluent 106a is generated from the first viral removal technique 130 and a second viral contaminant effluent 106b is generated from the second viral removal technique 132. The viral contaminant effluents 106a,b may be further processed separately or may be combined for such further processing, for example for analysis, waste treatment and/or disposal. Such purification processing 104 as illustrated in FIG. 2 may be used, for example, to evaluate efficacy of a unit operation of the biological medical product preparation process including multiple viral removal techniques for viral clearance across the unit operation. Alternatively, or additionally, each such different viral removal technique as illustrated in FIG. 2 may be evaluated individually for viral clearance, and the different evaluations may be combined to provide an overall evaluation of efficacy provided by the multiple viral removal techniques.

Figure 3:
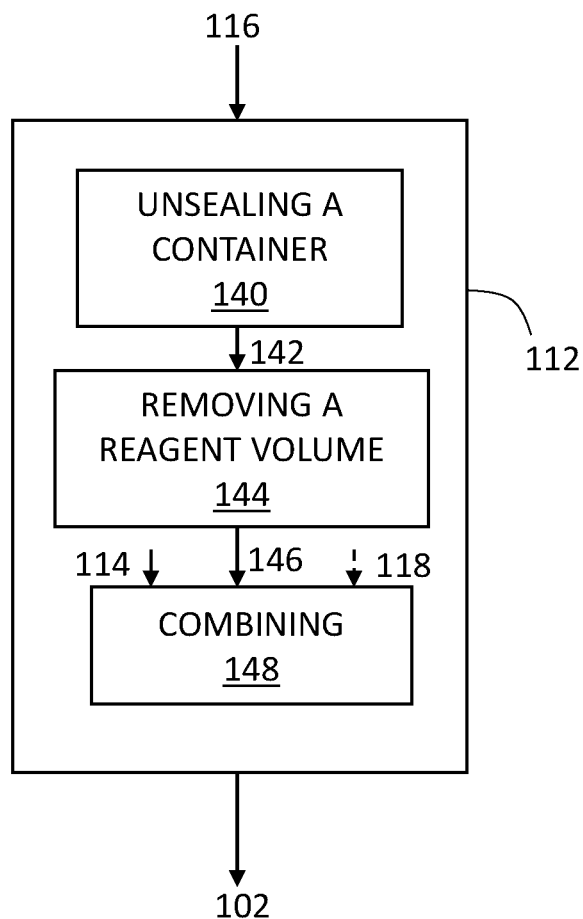
FIG. 3 is a process diagram illustrating some example embodiments of more specific processing within the general processing context of FIG. 1.

Reference is now made primarily to FIGS. 1 and 3. For convenience and quality control, the viral standard solution 116, having known compositional characteristics, may be provided in the form of a pre-packaged, sealed container. The container may have exteriorly observable viral standard indicia including identity of the viral particles in the fluorescent viral particles of the viral standard solution 116 and an analytically quantified number concentration of the fluorescent viral particles. The viral standard indicia may include other information about the viral standard solution and/or components of the viral standard solution 116, for example as described elsewhere herein. FIG. 3 illustrates an example of embodiment of some specific processing that may be included in the processing 112 of FIG. 1, when the viral standard solution 116 is provided in such a sealed container. As illustrated in FIG. 3, the processing 112 includes processing 140 of unsealing a sealed container, to provide access to the viral standard solution 116 in a now unsealed container 142. The processing 140 is followed by processing 144 of removing a reagent volume of the viral standard solution from the unsealed container 142. Following the processing 144, a removed reagent volume 146 of the viral standard solution 116 is subjected to processing 148 including combining the reagent volume 146 with a feed volume of the preliminary feed solution 114, and optionally also with reagent 118, to prepare the evaluation solution 102.

The processing of FIG. 1 provides flexibility to quickly evaluate different purification processing designs to remove viral contaminants, either as alternatives being considered for inclusion in the biological medical product preparation process or for use in different stages of the biological medical product preparation process. The processing of FIG. 1 also provides flexibility to quickly evaluate robustness of an identified purification processing alternative to remove multiple different types of viral contaminants.

In some implementations of the processing of FIG. 1, the evaluation solution 102 may include a plurality of different fluorescent viral particles, which include different viral particles and different fluorescent dyes conjugated with the different viral particles, wherein the different fluorescent viral particles have different fluorescent emission signatures, for example with peak fluorescent emissions at different electromagnetic wavelengths. The different viral particles may, for example, include viral characteristics of different virus families or of different viruses within a virus family. The different fluorescent dyes may be excited by a similar excitation wavelength (e.g., provided by a single laser tuned to a specific wavelength) or may be excited by different excitation wavelengths (e.g., provided by different lasers tuned to different wavelengths). Effectiveness of removal of each of the different types of fluorescent viral particles, as well as the overall effectiveness of removal of all fluorescent viral particles, may be evaluated during the processing 110 of FIG. 1. Such a plurality of different fluorescent viral particles may be provided together in a pre-prepared mixture in a single viral standard solution, for example in a single sealed container to be subjected to processing as shown in FIG. 3, or the different fluorescent viral particles may be provided separately, for example in separate, different viral standard solutions, with each such different viral standard solution including only a single type of fluorescent viral particles.

Figure 4:
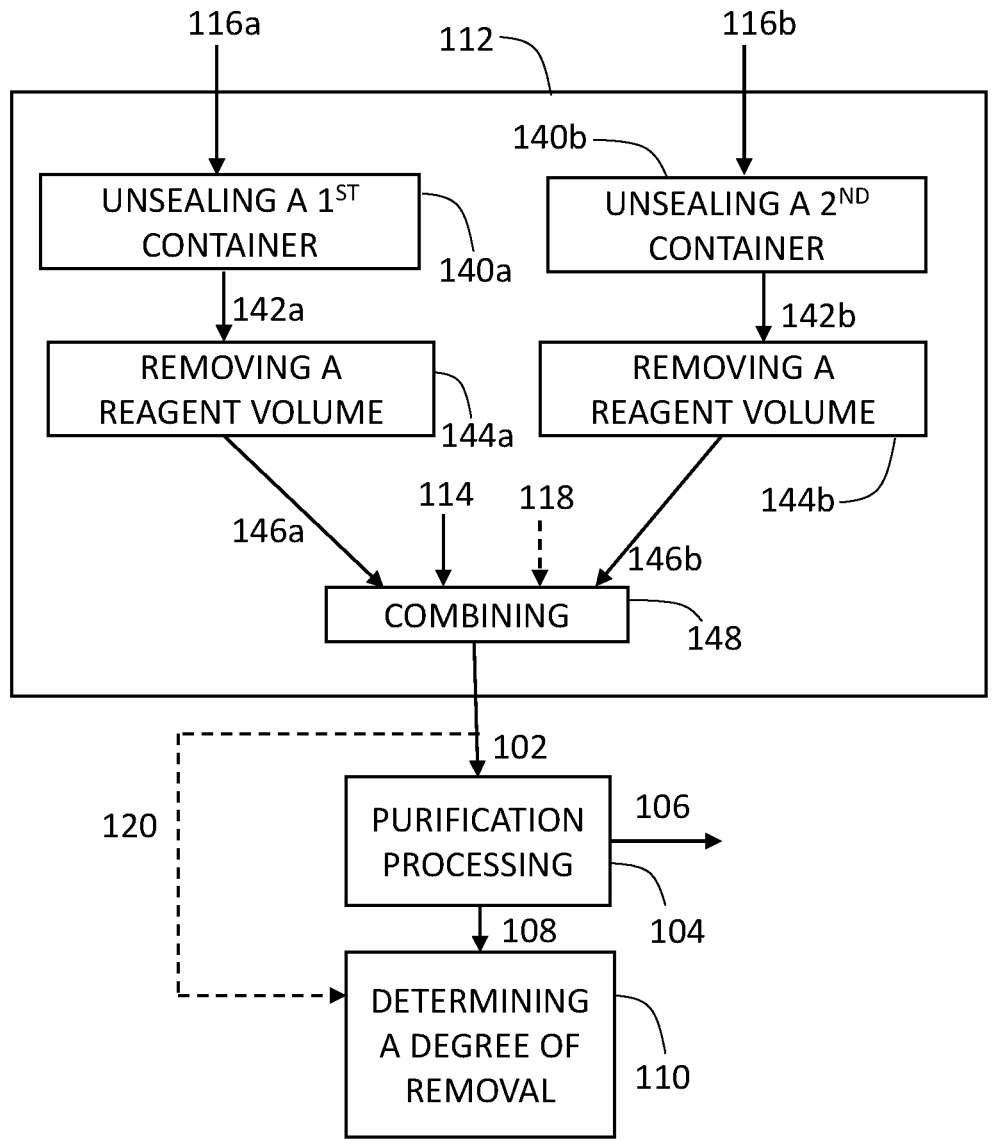
FIG. 4 is a process diagram illustrating some example embodiments of more specific processing within the general processing context of FIG. 1.

FIG. 4 illustrates an example of processing within the general processing approach of FIG. 1 utilizing a plurality of different fluorescent viral particles provided in separate viral standard solutions. During the processing 112 in the example of FIG. 4, a first viral standard solution 116a, containing first fluorescent viral particles, and a second viral standard solution 116b, containing second fluorescent viral particles, are separately processed through separate processing 140a,b of unsealing the respective sealed container and processing 144a,b of removing a reagent volume to obtain separate reagent volumes 146a,b of the different viral standard solutions for combination in the processing 148 with the preliminary feed solution 114 to prepare the evaluation solution 102 with both the first fluorescent viral particles from the first viral standard solution 116a and the second fluorescent viral particles from the second viral standard solution 116b. The viral contaminant effluent 106 from the purification processing 104 contains both first fluorescent viral particles and second fluorescent viral particles separated from the biological medical product during the purification processing 104 to prepare the treated solution 108, which includes the biological medical product purified to at least some degree relative to both the first fluorescent viral particles and the second fluorescent viral particles. During the processing 110 of FIG. 4, one or more samples of the treated solution 108 may be subjected to one or more analytical quantification techniques to provide individual qualifications for the first fluorescent viral particles and the second fluorescent viral particles in the treated solution 108. For example, a sample of the treated solution 108 may be subjected to flow cytometry with separate detectors to detect a first fluorescent emission signature from the first fluorescent viral particles and a second fluorescent emission signature from the second fluorescent viral particles and to determine a concentration of each of the first fluorescent viral particles and the second fluorescent viral particles in the treated solution 108, for comparison with corresponding quantities of the first fluorescent viral particles and the second fluorescent viral particles in the evaluation solution 102. Alternatively, first and second samples of the treated solution 108 may separately be subjected to analytical quantification, for example in different flow cytometry runs, to separately determine concentrations in the treated solution 108 for each of the first fluorescent viral particles and the second fluorescent viral particles, respectively. As shown in FIG. 4, a portion 120 of the evaluation solution 102 may optionally be provided to the processing 110, where the portion 120 of the evaluation solution 102 may be subjected to analytical quantification, to determine starting concentrations in the evaluation solution 102 for each of the first fluorescent viral particles and the second fluorescent virus particles, which for example may be performed in a combined flow cytometry evaluation or in separate flow cytometry evaluations for the first fluorescent viral particles and the second fluorescent viral particles in a manner as described for analytical quantification of the treated solution 108. The processing as illustrated in FIG. 4 may be used, for example, to evaluate the purification processing for removing virions of different viruses during the biological medical product preparation process to demonstrate the robustness of the biological medical product preparation process for clearance of viruses of different types.

Figure 5:
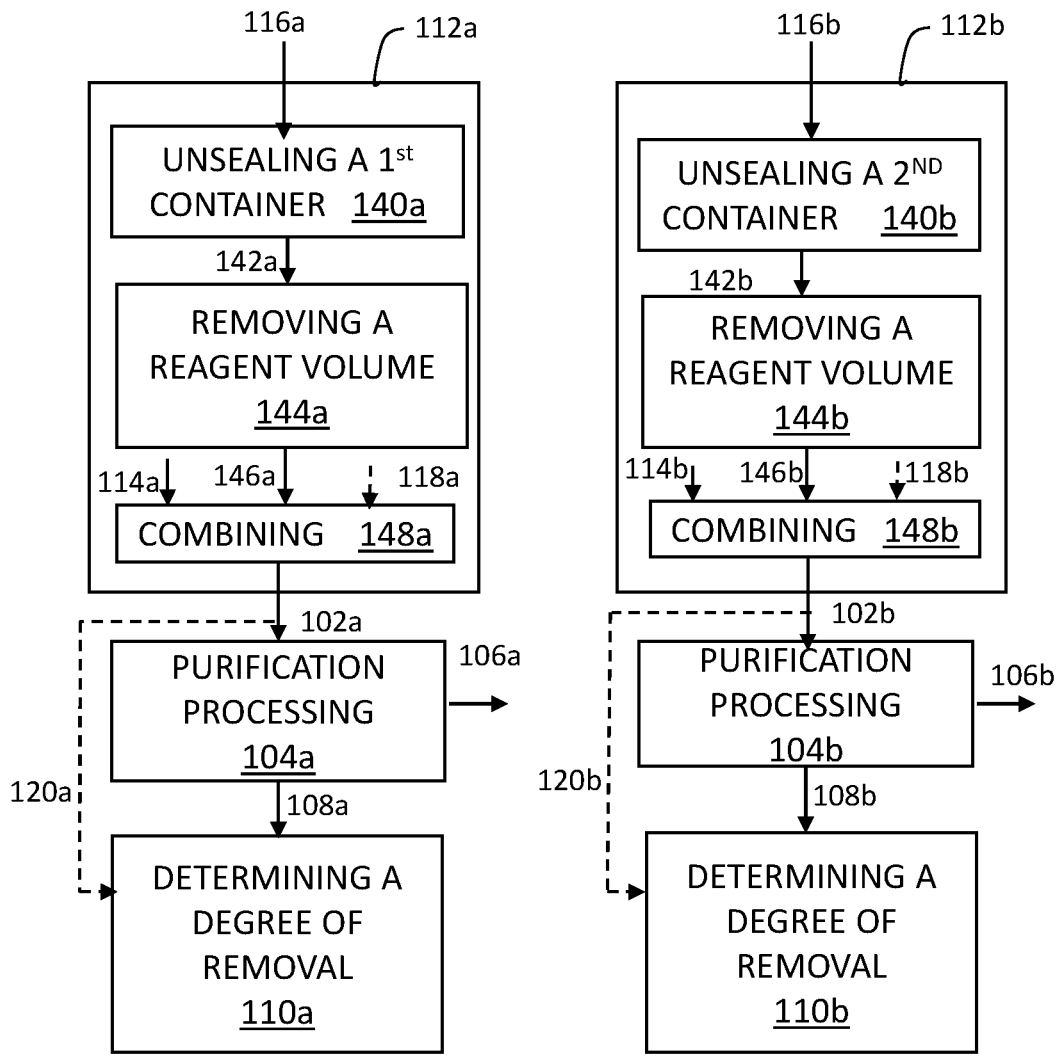
FIG. 5 is a process diagram illustrating some example embodiments of more specific processing within the general processing context of FIG. 1.

FIG. 5 illustrates an example of alternative processing to that shown in FIG. 4 for evaluating purification processing for removal of different types of viral contaminants. In the processing of FIG. 5 the first viral standard solution 116a and the second viral standard solution 116b are subjected to separate processing 112a and 112b to prepare separate evaluation solutions 102a and 102b. As seen in FIG. 5, the processing for each of the first viral standard solution 116a and the second viral standard solution 116b is the same as shown in FIG. 4 to prepare first and second reagent volumes 146a and 146b, respectively. However in the processing illustrated in FIG. 5, the different reagent volumes 146a and 146b, containing the first fluorescent viral particles and the second fluorescent viral particles, respectively, are not combined into a single evaluation solution 102 as shown in FIG. 4, but rather are used to prepare and separately process the separate evaluation solutions 102a,b through separate processing sequences of purification processing 104a,b to prepare separate treated solutions 108a,b. The treated solutions 108a,b are separately processed in processing 110a,b of determining a degree of removal of each of the first fluorescent viral particles and the second fluorescent viral particles from the respective evaluation solutions 102a,b. As shown in FIG. 5, portions 120a,b of the evaluation solutions 102a,b may be provided for use in the respective steps 110a,b for determining a degree of removal of the respective first or second fluorescent viral particles, as the case may be. The processing of FIG. 5 may be used, for example, to separately evaluate effectiveness of viral contaminant removal of different potential viral contaminants, represented by the different fluorescent viral particles, by the same purification processing of a biological medical product preparation process.

Figure 6:
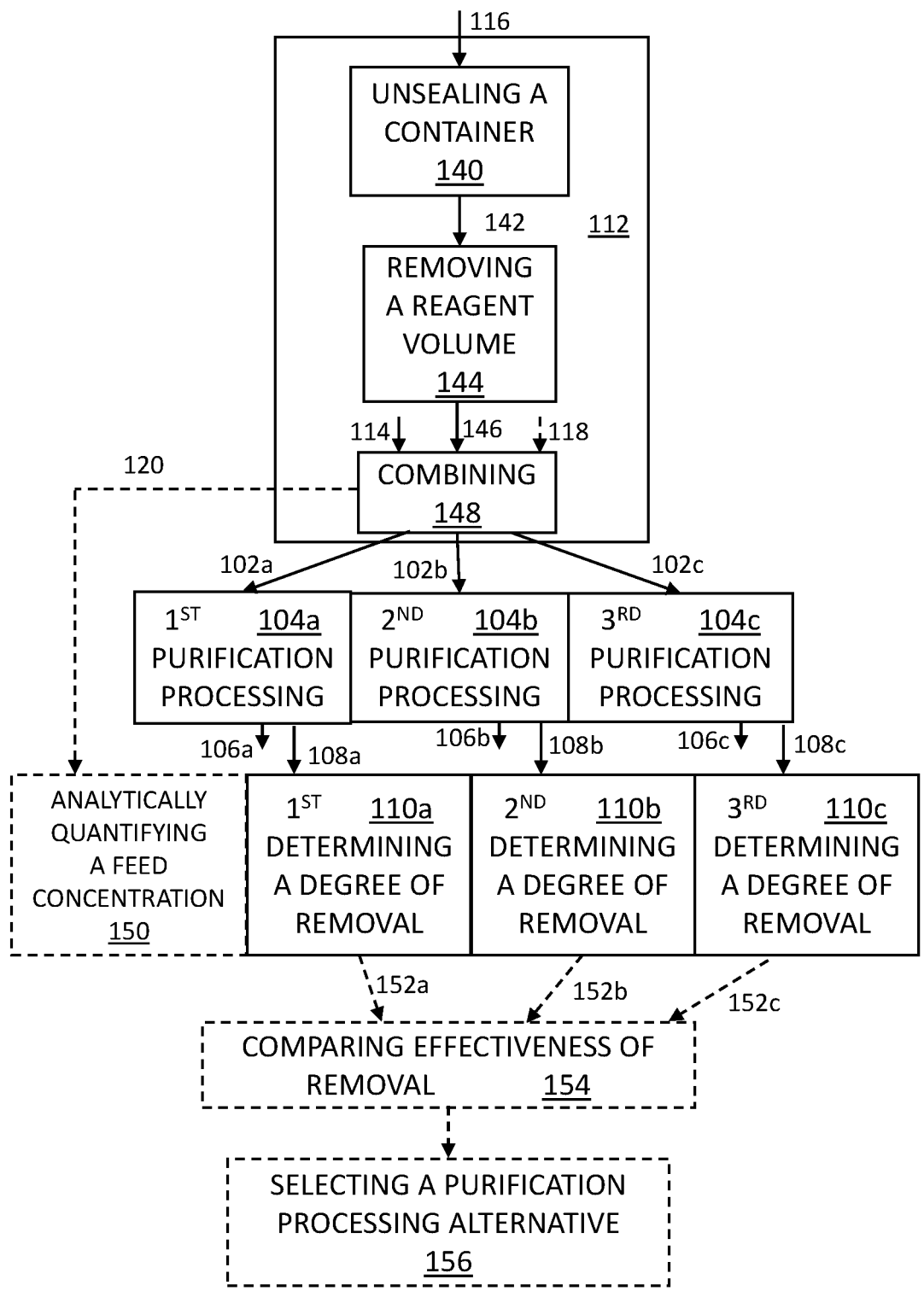
FIG. 6 is a process diagram illustrating some example embodiments of more specific processing within the general processing context of FIG. 1.

FIG. 6 illustrates a further example of flexibility of processing within the general processing approach of FIG. 1 to quickly evaluate the effectiveness for viral contaminant removal of a plurality of different purification processing alternatives, with the specific example of FIG. 6 including separate evaluation of three different purification processing schemes for viral clearance. The processing 112 of preparing the evaluation solution 102 is generally as that shown in FIG. 3, except that the resulting evaluation solution 102 is split into three separate aliquots identified in FIG. 6 as the separate evaluation solutions 102a,b,c. The separate evaluation solutions 102a,b,c are subjected to first purification processing 104a, second purification processing 104b and third purification processing 104c, respectively, to prepare the separate treated solutions 108a,b,c. A first treated solution 108a is subjected to first determining a degree of removal 110a of the fluorescent viral particles, a second treated solution 108b is subjected to second determining a degree of removal 110b of the fluorescent viral particles and a third treated solution 108c is subjected to third determining a degree of removal 110c of the fluorescent viral particles. As shown in FIG. 6, a portion 120 of the evaluation solution 102 from the combining 148 may be provided for use in the first determining a degree of removal 110a, the second determining a degree of removal 110b and the third determining a degree of removal 110c. In the example shown in FIG. 6, the portion 120 of evaluation solution is subjected to analytically quantifying a feed concentration 150 of the evaluation solution, which is applicable to processing for each of the different aliquots of the feed solutions 102a, 102b and 102c. The analytically quantifying a feed concentration 150 may include, for example, flow cytometry evaluation of one or more fluid sample prepared from the portion 120 of the evaluation solution 102.

The processing illustrated in FIG. 6 may be used to quickly and flexibly evaluate viral clearance performance at different stages within the biological medical product preparation process, in which case the first purification processing 104a, the second purification processing 104b and the third purification processing 104c may represent different purification processing schemes implemented at different stages during the biological medical product preparation process under evaluation. Alternatively, the first purification processing 104a, the second purification processing 104b, and the third purification processing 104c may each represent a different purification processing scheme being considered as alternatives for implementation in a particular stage or stages of the biological medical product preparation process. In this latter situation, the processing as shown in FIG. 6 permits rapid comparison of different alternative purification processing schemes under consideration for possible inclusion in the biological medical product preparation process. In that regard, FIG. 6 illustrates optional processing in which the results 152a,b,c from the first determining a degree of removal 110a, the second determining a degree of removal 110b and the third determining degree of removal 110c, respectively, may be used in optional processing 154 of comparing effectiveness of removal of the fluorescent viral particles by each of the first purification processing 104a, second purification processing 104b and third purification processing 104c, followed by processing 156 of selecting a purification processing alternative 156 from among the first purification processing 104a, the second purification processing 104b and the third purification processing 104c for use in the particular stage or stages of the biological medical material preparation process under consideration.

Because the processing illustrated in FIG. 6 prepares a larger batch of evaluation solution at one time, which is then aliquoted to prepare the separate feed solutions 102a,b,c, it is preferred in the processing of FIG. 6 that the first purification processing 104a, second purification processing 104b and third purification processing 104c be performed reasonably contemporaneously to avoid time-related differences between tests.

Figure 7:
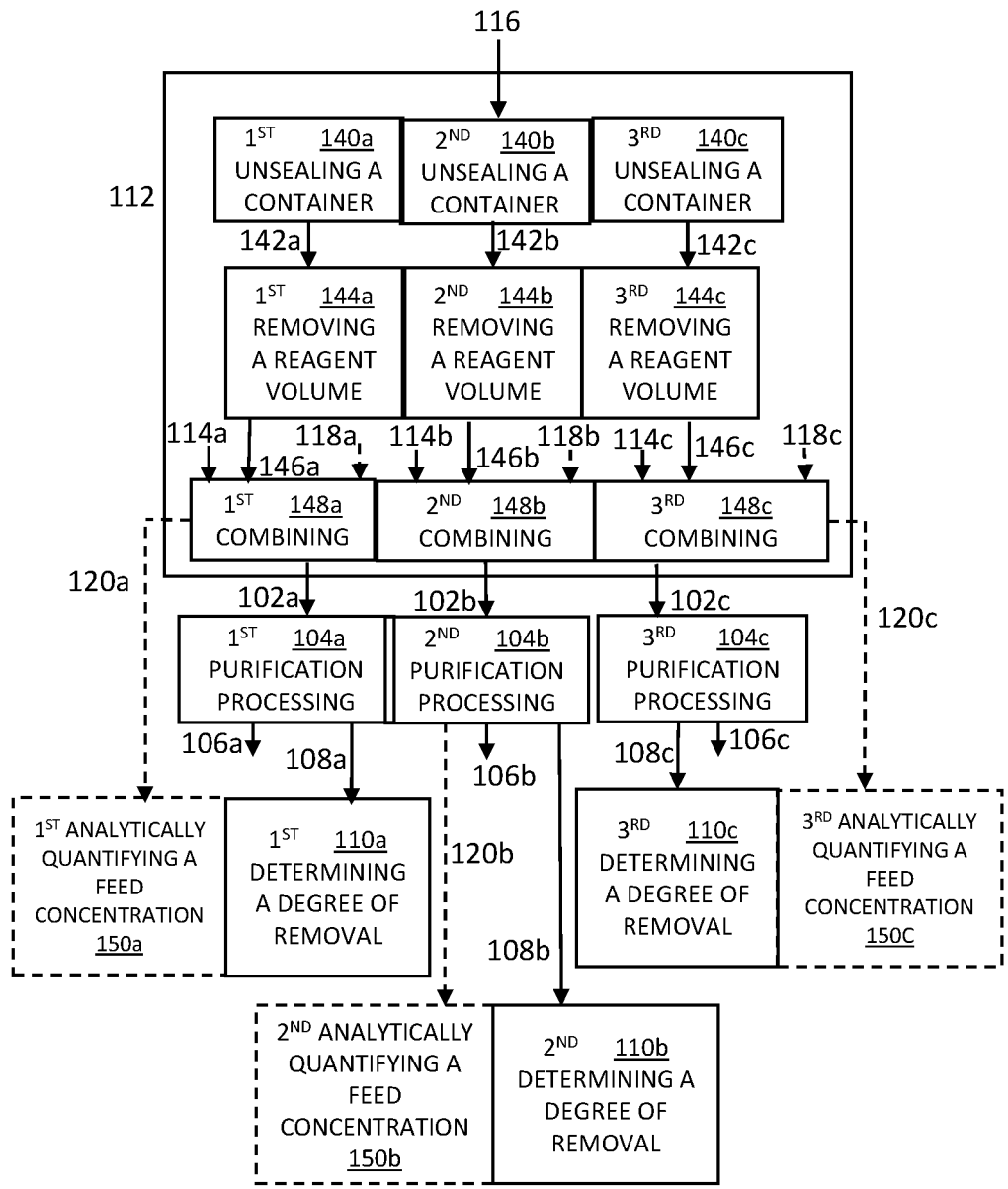
FIG. 7 is a process diagram illustrating some example embodiments of more specific processing within the general processing context of FIG. 1.

FIG. 7 shows an example of an alternative to the processing shown in FIG. 6 to evaluate multiple different purification processing schemes. The example processing of FIG. 7 includes the same first purification processing 104a, second purification processing 104b and third purification processing 104c on separate evaluation solutions 102a,b,c as illustrated in and discussed with respect to FIG. 6. However, in the processing of FIG. 7, the separate evaluation solutions 102a,b,c are individually prepared by separate sequences of processing during the general processing 112, rather than being aliquoted from a single master batch of evaluation solution 102. Consequently, as shown for the processing example in FIG. 7, separate portions 120a,b,c of evaluation solutions 102a,b,c may be provided separately for first analytically quantifying feed concentration 150a, second analytically quantifying feed concentration 150b and third analytically quantifying feed concentration 150c, corresponding to each of the first determining a degree of removal 110a, second determining a degree of removal 110b and third determining a degree of removal 110c, respectively. The processing example illustrated in FIG. 7 may be used instead of the example processing shown in FIG. 6 for evaluating between potential alternative purification processing schemes being considered for use in a particular stage or stages of the biological medical product preparation process or for evaluating different purification processing schemes identified for use in different stages of the medical product preparation process. Processing as shown in FIG. 7, however, may be preferred for use in situations when the first evaluation solution 102a, second evaluation solution 102b and third evaluation solution 102c are not processed reasonably contemporaneously. When the processing of FIG. 7 is used to evaluate between potential alternative purification processing schemes for use in a particular stage or stages of the biological medical product preparation process, the processing shown in FIG. 7 may be followed by the additional steps shown in FIG. 6 of comparing effectiveness of removal 154 and selecting a purification processing alternative 156, in a manner similar to the discussion above in relation to FIG. 6.

Any of evaluation solution 102, purification processing 104, viral contaminant waste effluent 106, treated solution 108, determining a degree of removal 110, preparing an evaluation solution 112, preliminary feed solution 114, viral standard solution 116, reagent 118, portion 120 of an evaluation solution, first viral removal technique 130, second viral removal technique 132, sealed container 140, unsealed container 142, removing a reagent volume 144, removed reagent volume 146, combining 148, analytically quantifying a feed concentration 150, results 152, comparing effectiveness of removal 154 and selecting a purification processing alternative 156 may be or have any features described for such a feature elsewhere in this disclosure, including without limitation in the SUMMARY section provided above, the numbered Implementation Examples presented below or the appended claims.

Figure 8:
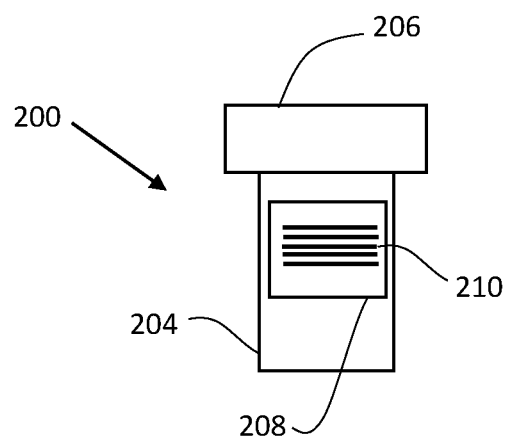
FIG. 8 illustrates an example embodiment of a viral standard product of a second aspect of this disclosure.
Figure 9:
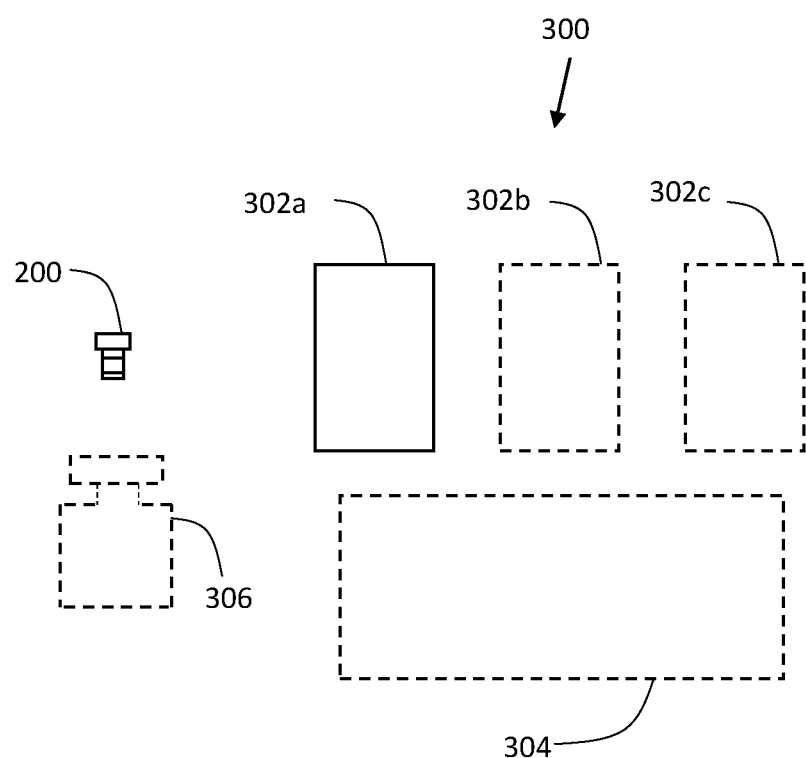
FIG. 9 illustrates some example embodiments of a kit of a third aspect of this disclosure.

Reference is now made to FIGS. 8 and 9 illustrating examples of a viral standard product and a kit, corresponding to second and third aspects of the disclosure summarized above.

FIG. 8 illustrates an example viral standard product 200 including a sealed container in which is disposed a volume of a viral standard solution. The sealed container includes a container body 204 and a cap 206 engaged with and sealing to the container body 204. The cap 206 is manipulable, for example by twisting, to unseal the sealed container and to remove the cap 206 to provide access to the viral standard solution in the container body 204. After the cap 206 is removed, measured volumes of the viral standard solution may be removed from the container body 204, for example by pipetting, for use in a method for viral clearance evaluation as disclosed herein, for example in the first aspect of this disclosure. The sealed container includes a label 208 including exteriorly observable viral standard indicia 210 with information concerning the viral standard solution contained within the sealed container. By the indicia being exteriorly observable, it is meant that the information in the indicia may be discerned by observation, which may be a human or machine observer, from outside of the container. The viral standard indicia 210 may be presented in a written form readable by a human user (e.g., written words and/or numbers) and/or may be presented in a coded machine-readable format (e.g., a scannable barcode). Viral standard indicia 210 will preferably include at least the identity of the viral particles of the fluorescent viral particles in the viral standard solution and an analytically quantified number concentration of the fluorescent viral particles in the viral standard solution. The viral standard indicia 210 may also include any other information or combinations of information as disclosed elsewhere herein and the sealed container may be or have any features disclosed elsewhere herein, including without limitation in the SUMMARY section presented above, the numbered Implementation Examples presented below or the appended claims.

FIG. 9 illustrates an example kit 300 for use in viral clearance evaluation for a biological medical product preparation process, for example in a method of the first aspect of this disclosure. The example kit 300 illustrated in FIG. 9 includes the viral standard product 200 illustrated in and described in relation to FIG. 8. The kit 300 as illustrated in FIG. 9 also includes at least one virus removal device 302a, and optionally includes a plurality of virus removal devices (illustrated in FIG. 9 as optionally including two additional viral removal devices 302b,c) for testing removal of the fluorescent viral particles during purification processing of a method for viral clearance evaluation. Some or all of the virus removal devices 302a,b,c may be the same, but preferably at least some of, and more preferably all of, the virus removal devices 302a,b,c are different viral removal devices each comprising a different virus removal technique. As illustrated in FIG. 9, the kit 300 may optionally include an analytical instrument 304 for analytically quantifying a number concentration of fluorescent viral particles in a liquid solution as part of a viral clearance evaluation (e.g., in an evaluation solution and or in a treated solution). In one preferred implementation the analytical instrument 304 is a flow cytometer. Preferably, the analytical instrument 304 is the same type of analytical instrument as was used to determine the analytically quantified number concentration of the fluorescent virus particles in the viral standard solution. When the analytical instrument 304 is a flow cytometer, one preferred flow cytometer is the Virus Counter® 3100 flow cytometer (Sartorius Stedim Biotech), which is specifically designed for quantification of virus-size particles with a fluorescent label. Also as shown in FIG. 9, the example kit 300 may optionally include a sealed reagent container 306 containing a liquid formulation reagent for use in a viral clearance evaluation (e.g., a buffer solution for use in preparation of evaluation solutions containing fluorescent viral particles from the viral standard solution and biological medical product for the method of the first aspect of this disclosure as summarized above).

Figure 10:
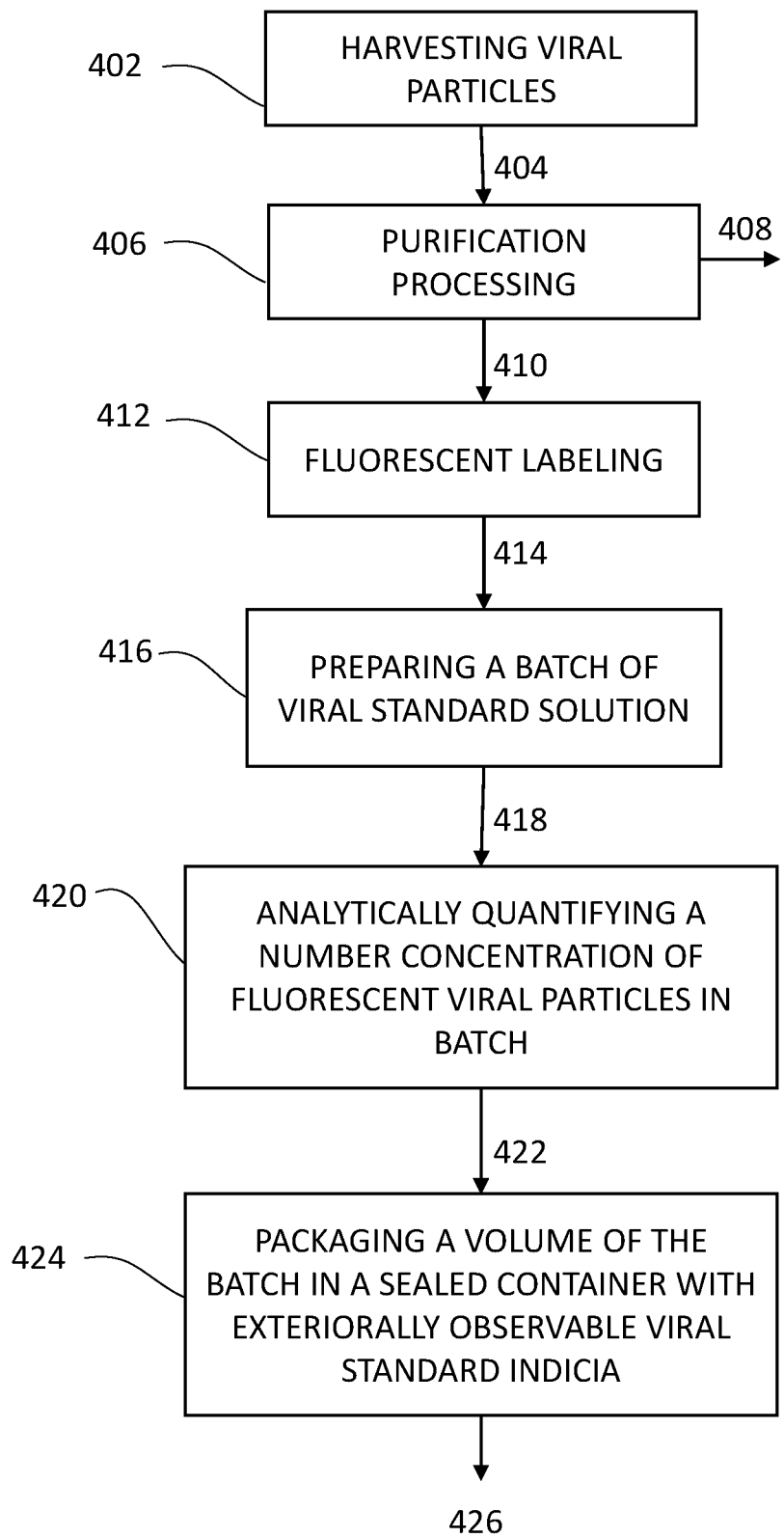
FIG. 10 is a process diagram illustrating processing of some example embodiments of a method of preparing a viral standard product of a fourth aspect of this disclosure.

FIG. 10 includes a generalized process diagram illustrating an example method for making a viral standard product, corresponding to a fourth aspect of this disclosure as summarized above. A result of the method of FIG. 10 may be, for example, the viral standard product 200 illustrated in FIGS. 8 and 9. The method illustrated in FIG. 10 includes harvesting viral particles 402, during which viral particles targeted for preparation of fluorescent viral particles are recovered from a viral particle production operation in harvested material 404. The viral particle production operation may for example involve a cell culture or fermentation operation generating the viral particles, and the harvested material 404 may include cell culture media, fermentation media and/or cell lysate solution including the desired viral particles. The viral particles may be virions, virus-like particles or other nanoparticles with a viral epitope. Some preferred viral particles are virus-like particles, for example from a cell line expressing viral proteins that assemble into the virus-like particles.

The harvested material 404 is subjected to purification processing 406, during which the viral particles are at least partially cleaned of contaminants from the production operation, for example cell debris. The purification processing 406 may include any number of purification techniques for separating viral particles from contaminants. For example, such purification techniques may include any of the techniques described for removal of the fluorescent viral particles from the biological medical product during the method of the first aspect of this disclosure for viral clearance evaluation for a biological medical product preparation process. Typical purification techniques that may be used during the purification processing include, for example centrifugation (e.g., to sediment cell debris), ultracentrifugation (e.g., to sediment viral particles), filtration (e.g., to pass viral particles in filtrate or to retain viral particles in retentate), precipitation (e.g., of viral particles or debris), chromatography (e.g., affinity chromatography for selective capture of viral particles) and membrane separation techniques (e.g., active or inactive membranes). A membrane separation technique may in one example include dialysis. A waste effluent 408 is shown being removed from the purification processing 406 in FIG. 10. A purified process solution 410 containing the viral particles in a more purified form is subjected to fluorescent labeling 412, during which a fluorescent dye is conjugated to the viral particles to convert viral particles into fluorescent viral particles.

The fluorescent labeling 412 may include reacting a reactant molecule comprising a fluorescent dye with a reactive group on a viral protein of the viral particles to covalently attach the fluorescent dye to the viral particle. One preferred reactive group is a primary amine, which may be a primary amine on a lysine amino acid residue. The reactant molecule, for example, may be or have properties as described in the Summary section, the numbered Implementation Examples presented below or the appended claims. In some preferred implementations the reactant molecule comprises a succinimidyl ester, which may for example preferably be a N-hydroxysuccinimide ester. Some example amine-reactive groups for the reactive molecule are described in "Protein Cross-Linkers Handbook and Selection Guide", G-Biosciences, available at info2.gbiosciences.com; "Thermo Scientific Crosslinking Technical Handbook", ThermoFisher Scientific, available at www.therofisher.com; and Banks, Peter R., et al., "Comparison of Three Common Amine Reactive Fluorescent Probes Used for Conjugation to Biomolecules by Capillary Zone Electrophoresis", Bioconjugate Chem. 1995, 6, 447-458; each and every one of which is incorporated herein by reference for all purposes. Advantageously, the fluorescent viral particles may only be marginally increased in size relative to the original viral particle prior to the fluorescent labeling 412. In that regard, the added moiety with the fluorescent dye may have a relatively small molecular mass, often no larger than 2,500 Daltons, and the fluorescent labeled particles may be increased in size relative to the original viral particles by only 4 nanometers or less, and often by much less. This is significantly different, for example, than labelling of viral particles with fluorescent antibody stains, which may increase particle size on the order of 15 nanometers. To maintain the fluorescent labeled particles as close as possible to the size of the original viral particles, the fluorescent viral particles are preferably in the absence of labeling with any fluorescent antibody stain. The fluorescent labeled particles are also preferably in the absence of incorporation of green fluorescent protein (GFP) in viral particle genome, as incorporation of GFP can significantly increase viral particle size.

As also discussed previously, significant advantages result from using the fluorescent viral particles of this disclosure for virus clearance evaluation. Because the fluorescent viral particles are similar in size to corresponding unlabeled viral particles, they can be used from beginning to end in the viral clearance evaluation process without need for chemical modification. Unlike other test particles used for viral clearance evaluation, there is no need to stain treated solutions with a fluorescent stain following purification processing for analytical quantification of viral clearance effectiveness. Avoiding such post-processing staining removes the burden of performing that step and testing variability as a consequence of chemistry associated with such staining. For example, use of the fluorescent viral particles removes variability in antibody stain binding as a consequence of different treated solution chemistries, and removes a need to manipulate treated solution chemistry in preparation for fluorescent staining. The fluorescent viral particles provide a testing standard that remains stable in different test solution chemistries and across the different analytical quantification techniques. The treated solution as resulting from the purification processing may be subjected directly to quantification analysis, preferably by flow cytometry, without need for intermediate manipulation of the treated solution. Because the fluorescent dye is covalently attached to the viral particles, the fluorescent dye is strongly bound to the viral particles and remains intact on the fluorescent viral particles for analytical quantification of the fluorescent viral particles, even after the stress of being subjected to the purification processing. Accordingly, the fluorescent viral particles advantageously provide a robust standard for use with a wide variety of viral particles of interest for testing, and across a variety of purification processing alternatives that may be tested, as part of a viral clearance evaluation.

Continuing with reference to FIG. 10, a labeled process solution 414 including the fluorescent viral particles is recovered and subjected to processing 416 of preparing a batch of viral standard solution including the fluorescent viral particles. During the processing 416, the fluorescent viral particles are formulated in a final desired form in a liquid medium with desired properties (e.g., salt concentration, buffer system, pH and additives) for the viral standard solution in the final packaged viral standard product. Processing in step 416 may include, for example, purification processing of the fluorescent viral particles (e.g., to separate the fluorescent viral particles from residual unbound dye molecules and other chemicals from the fluorescent labeling 412) to a purified form, concentrating the fluorescent viral particles to a higher concentration desired for the viral standard solution and/or to disperse the fluorescent viral particles in the desired liquid medium for the final viral standard solution.

After preparing the batch 418 of viral standard solution with desired final liquid medium and other properties resulting from processing 416, then the batch 418 of viral standard solution is subjected to processing 420 of analytically quantifying a number concentration (e.g., particles per milliliter) of the fluorescent viral particles in the batch. This may be accomplished by taking one or more representative fluid samples from the batch 418 and subjecting the representative fluid samples to an analytical quantification technique, preferably flow cytometry, to quantify the number concentration. The analytically quantified batch 422 is then subjected to processing in step 424 of packaging a volume of the batch in a sealed container to prepare a viral standard product 426, with the sealed container having exteriorly observable viral standard indicia containing information about the batch. Such an exteriorly observable viral standard indicia may be provided, for example, on a label on the sealed container. The exteriorly observable viral standard indicia may be placed on a container prior to or after disposing a volume of the batch in the container and prior to or after sealing the container. The exteriorly observable viral standard indicia will preferably include at least the identity of the viral particles and the analytically quantified number concentration of the fluorescent viral particles.

Figure 11:
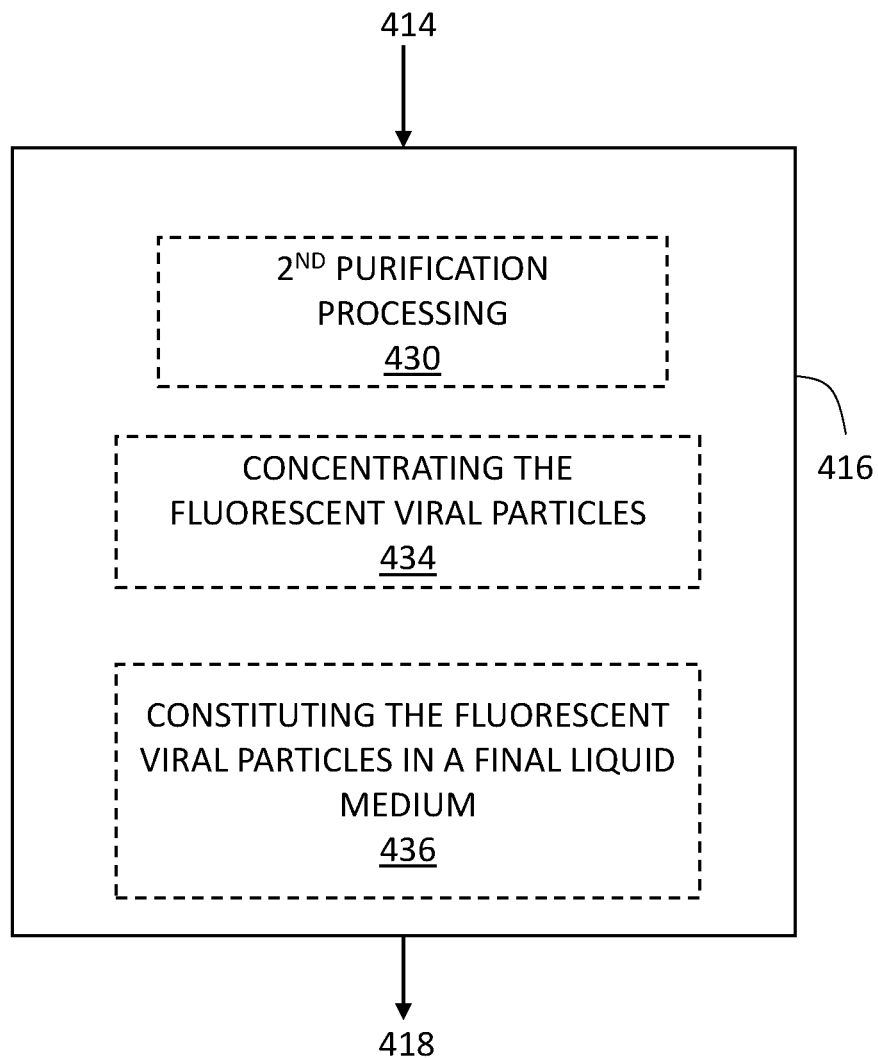
FIG. 11 is a process diagram illustrating some example embodiments of more specific processing within the general processing context of FIG. 10.

FIG. 11 shows some example processing that may be performed during the processing 416 of FIG. 10. As illustrated in FIG. 11, the processing 416 may include second purification processing 430 to prepare a more purified labeled process solution having a higher purity level of the fluorescent viral particles. The second purification processing may include one or more purification techniques, for example using any of the purification techniques described for the purification processing 408. During the second purification processing 430, most or even essentially all unbound (unconjugated) fluorescent dye is separated from the fluorescent viral particles. Also as illustrated in the example of FIG. 11, the processing 416 may include processing 434 of concentrating the fluorescent viral particles to a higher concentration in the batch 418 of viral standard solution. The processing 434 may include one or more concentration techniques, such as for example centrifugation, filtration, affinity separation, and precipitation, which may be combined with reconstitution of the fluorescent viral particles in a new liquid medium to a higher concentration than in the labeled process solution 414. Also as illustrated in FIG. 11, the processing 416 may include processing 436 of constituting the fluorescent viral particles in a final liquid medium for the standard product batch 418, and consequently in the viral standard product 426. The processing 436 may include changing out the liquid medium or adding reagents (e.g., for pH adjustment and non-agglomeration of fluorescent viral particles) to prepare the batch 418 with a liquid dispersion medium for the fluorescent viral particles desired for the final viral standard product 426. As may be appreciated, the processing 430, 434 and 436 may be performed in any order and may overlap in processing. For example, filtration, centrifuging, affinity separation, or precipitation may accomplish both a level of purification of the fluorescent viral particles and concentration of the fluorescent viral particles to a higher concentration than in the labeled process solution 414, and may prepare the fluorescent labeled particles for reconstitution in a desired liquid medium for the final viral standard product 426. In some preferred implementations, the batch 418 of viral standard solution is substantially free of any unbound fluorescent dye, that is substantially free of any fluorescent dye not conjugated to viral particles, although the viral standard solution may have a very small residual concentration of the unbound fluorescent dye. As will be appreciated, the viral standard solution will have the same composition in the batch 418 and the viral standard product 426, and may also be the composition of the viral standard solution 116 illustrated and discussed in relation to any of FIGS. 1-7 and/or contained in the viral standard product 200 illustrated in and discussed in relation to FIGS. 8 and 9.

Figure 12:
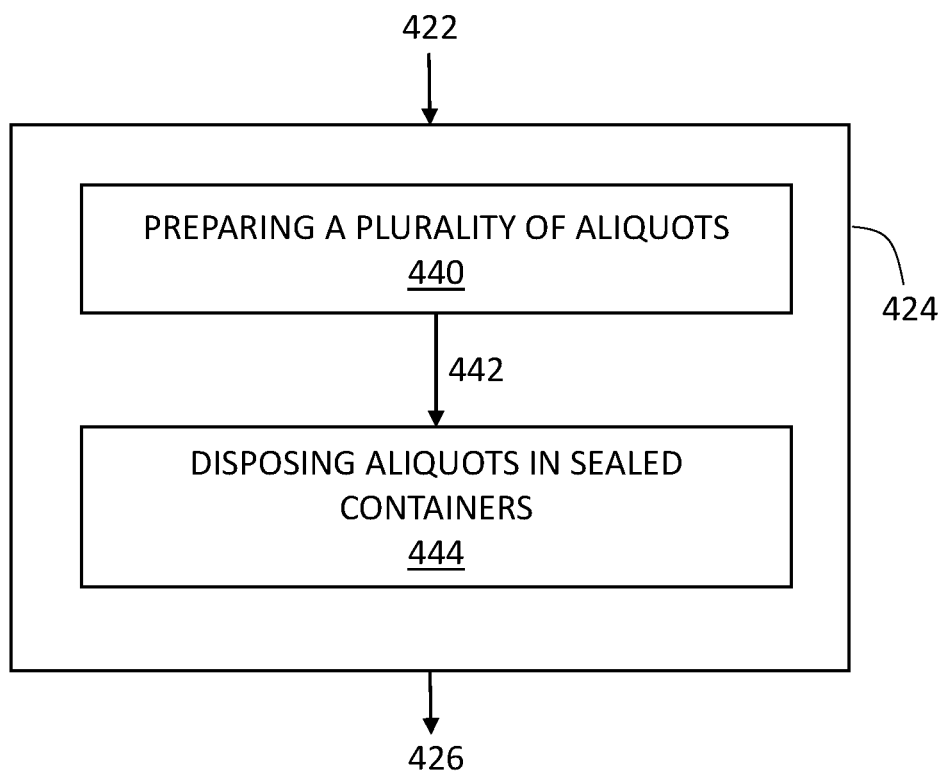
FIG. 12 is a process diagram illustrating some example embodiments of more specific processing within the processing context of FIG. 10.

FIG. 12 shows an example of some operations that may be performed during the processing 424 of the general processing of FIG. 10. As illustrated in FIG. 12, the processing 424 includes processing 440 of preparing a plurality of aliquots 442 from the analytically quantified batch 422, followed by processing 444 of disposing the aliquots 442 in separate sealed containers having the exteriorly observable viral standard indicia for the analytically quantified batch 422. The viral standard product 426 includes a plurality of the sealed containers each including a different one of the aliquots 442.

Implementation Examples

Some other contemplated example combinations for use in connection with implementation of the various aspects of this disclosure, with or without additional features as disclosed above or elsewhere herein, are summarized in the numbered paragraphs presented below, and in the appended claims:

1. A method for viral clearance evaluation for a biological medical product preparation process, the method comprising:

subjecting an evaluation solution to purification processing to prepare a treated solution, wherein the evaluation solution comprises a biological medical product and fluorescent viral particles, and wherein the purification processing comprises a viral removal technique for separation of a viral contaminant from the biological medical product; and determining a degree of removal of the fluorescent viral particles between the evaluation solution and the treated solution; and wherein the fluorescent viral particles comprise viral particles and a fluorescent dye conjugated to the viral particles.

2. The method of paragraph 1, wherein the purification processing comprises a said removal technique selected from the group consisting of chromatography (optionally, column chromatography, planar chromatography, membrane chromatography, affinity chromatography, ion exchange chromatography, size-exclusion chromatography, reversed-phase chromatography, hydrophobic interaction chromatography, and multi-dimensional chromatography, e.g., two-dimensional chromatography), filtration (optionally, ultrafiltration or nanofiltration), centrifugation (optionally, ultracentrifugation), membrane separation (optionally, affinity membrane separation), dialysis and combinations thereof.

3. The method of either one of paragraph 1 or paragraph 2, wherein the purification processing comprises displacement chromatography and collection of the biological medical product at higher purity in displacement solution effluent from the displacement chromatography.

4. The method of either one of paragraph 1 or paragraph 2, wherein the purification processing comprises elution chromatography and collection of the biological medical product at higher purity in an elution solution effluent from the elution chromatography.

5. The method of any one of paragraphs 1-4, wherein the purification processing comprises filtration and collection of the biological medical product at higher purity in filtrate of the filtration.

6. The method of any one of paragraphs 1-5, wherein the purification processing comprises affinity separation, optionally selected from the group consisting of affinity chromatography and affinity membrane separation.

7. The method of any one of paragraphs 1-6, wherein the purification processing comprises membrane separation of the fluorescent viral particles from the biological medical product.

8. The method of any one of paragraphs 1-7, wherein the purification processing comprises a plurality of different said removal techniques arranged in series to prepare the treated solution.

9. The method of any one of paragraphs 1-8, wherein the evaluation solution comprises a concentration of the fluorescent viral particles of at least $1\times10^7$ particles per milliliter, preferably at least $1\times10^8$ particles per milliliter, and more preferably at least $1\times10^9$ particles per milliliter.

10. The method of any one of paragraphs 1-9, wherein the evaluation solution comprises a concentration of the fluorescent viral particles of up to $1\times10^{12}$ particles per milliliter.

11. The method of any one of any one of paragraphs 1-10, wherein the biological medical product is selected from the group consisting of a protein, a nucleic acid, a vaccine, a blood component, a blood derivative and a plasma derivative.

12. The method of any one of paragraphs 1-11, wherein the biological medical product is a macromolecule of molecular mass in a range of from 10,000 to 150,000 Daltons.

13. The method of any one of paragraphs 1-12, wherein the biological medical product is selected from the group consisting of a hormone, an interferon, a monoclonal antibody and a recombinant DNA-derived product.

14. The method of any one of paragraphs 1-13, wherein the evaluation solution includes the biological medical product at a concentration in a range of from 20 µg/mL to 100 mg/mL.

15. The method of any one of paragraphs 1-14, wherein the biological medical product is derived from a cell culture of a human, mammalian, avian or insect origin.

16. The method of any one of paragraphs 1-14, wherein the biological medical product is derived from a cell culture derived from bacteria or yeast.

17. The method of any one of paragraphs 1-14, wherein the biological medical product is derived from a hybridoma cell culture.

18. The method of paragraph either one of paragraphs 15-17, wherein the cell culture is of a characterized cell line.

19. The method of paragraph 18, wherein the characterized cell line is genetically engineered.

20. The method of any one of paragraphs 1-14, wherein the biological medical product is derived from microbial fermentation.

21. The method of any one of paragraphs 1-14, wherein the biological medical product is derived from in vivo cell growth.

22. The method of any one of paragraphs 1-21, comprising;
subjecting each of a plurality of different said evaluation solutions, each comprising the biological medical product and the fluorescent viral particles, to a different said purification processing to prepare different said treated solutions, wherein each different said purification processing includes a different said viral removal technique; and
determining a said degree of removal of the fluorescent viral particles between each said corresponding pair of a said evaluation solution and a said treated solution for each different said purification processing.

23. The method of paragraph 22, wherein at least two of the different said evaluation solutions have the same composition for evaluation of viral clearance alternatives for the different said evaluation solutions having the same composition.

24. The method of either one of paragraph 22 or paragraph 23, wherein at least two of the different said evaluation solutions have different compositions for evaluation of viral clearance at different stages of the biological medical product preparation process.

25. The method of any one of paragraphs 1-24, wherein;
the fluorescent viral particles are first said fluorescent viral particles comprising first said viral particles and first said fluorescent dye;
a said evaluation solution comprises second said fluorescent viral particles comprising second said viral particles and second said fluorescent dye
the first said viral particles have a first viral epitope of a first virus and the second said viral particles have a second viral epitope of a second virus different than the first virus;
the first fluorescent dye has a first fluorescent emission signature and the second fluorescent dye has a second fluorescent emission signature, different than the first fluorescent emission signature; and
the method comprises second determining a degree of removal of the second said fluorescent viral particles between the evaluation solution and the treated solution.

26. A method of any one of paragraphs 1-24, wherein;
the evaluation solution is a first said evaluation solution, and the fluorescent viral particles are first said fluorescent viral particles comprising first said viral particles and first said fluorescent dye, the treated solution is a first said treated solution and the determining a degree of removal is a first said determining a degree of removal; and the method further comprises:

subjecting a second said evaluation solution to the purification processing to prepare a second said treated solution, wherein the second said evaluation solution comprises second said fluorescent particles comprising second said viral particles, different than the first said viral particles, and second said fluorescent dye (which second said fluorescent dye may be the same or different than the first said fluorescent dye), and wherein the first fluorescent dye has a first fluorescent emission signature and the second fluorescent dye has a second fluorescent emission signature (which second said fluorescent emission signature may the same or different than the first said fluorescent emission signature); and second said determining a degree of removal of the second said fluorescent viral particles between the second said evaluation solution and the second said treated solution;

and optionally, wherein the first said viral particles and the second said viral particles are of different virus families.

27. The method of any one of paragraphs 1-26, wherein the evaluation solution comprises biological contaminants, other than the fluorescent viral particles, representative of the biological medical product preparation process.

28. The method of paragraph 27, wherein the biological contaminants comprise lysate cell debris.

29. The method of either one of paragraph 27 or paragraph 28, wherein the biological contaminants comprise an enzyme.

30. The method of any one of paragraphs 27-29, wherein the evaluation solution comprises the biological contaminants at a concentration in a range of from 0.7 mg/mL to 7.0 mg/mL.

31. The method of any one of paragraphs 27-30, wherein the treated solution has a lower concentration of the biological contaminants than the evaluation solution.

32. The method of any one of paragraphs 1-31, wherein the determining a degree of removal of the fluorescent viral particles comprises determining a feed concentration of the fluorescent viral particles in the evaluation solution and a residual concentration of the concentration of the fluorescent viral particles in the treated solution.

33. The method of any one of paragraphs 1-32, wherein the determining a degree of removal of the fluorescent viral particles comprises subjecting a sample of the treated solution to an analytical technique to analytically quantify a residual concentration of the fluorescent viral particles in the evaluation solution.

34. The method of paragraph 33, wherein the analytical technique comprises flow cytometry evaluation.

35. The method of paragraph 33, wherein the analytical technique comprises a member selected from the group consisting of nanoparticle tracking analysis, imaging and microscopy, and preferably nanoparticle tracking analysis.

36. The method of any one of paragraphs 33-35, wherein the analytical technique has a quantification limit to quantify the residual concentration of a level of at least a 3 log reduction relative to the feed concentration, and preferably at least a 4 log reduction relative to the feed concentration.

37. The method of any one of paragraphs 33-36, wherein the analytical technique comprises counting the fluorescent viral particles in the sample volume of the treated solution with a lower quantification limit of at least as low as (not greater than) $1\times10^4$ particles per milliliter or smaller, and preferably with a lower quantification limit of at least as low as (not greater than) $1\times10^3$ particles per milliliter or smaller.

38. The method of any one of paragraphs 1-37, wherein the determining a degree of removal of the fluorescent viral particles comprises subjecting a sample volume of the evaluation solution to an analytical technique to analytically quantify a feed concentration of the fluorescent viral particles in the evaluation solution.

39. The method of paragraph 38, wherein the analytical technique comprises flow cytometry evaluation, optionally including subjecting to flow cytometry a series of diluted samples prepared from the evaluation solution.

40. The method of paragraph 38, wherein the analytical technique comprises a member selected from the group consisting of nanoparticle tracking analysis, imaging, and microscopy, and preferably nanoparticle tracking analysis.

41. The method of any one of paragraphs 1-40, comprising preparing the evaluation solution, wherein the preparing the evaluation solution comprises:

combining a feed volume of a preliminary feed solution comprising the biological medical product with a reagent volume of a viral standard solution comprising the fluorescent viral particles dispersed in a standard liquid medium at an analytically quantified number concentration.

42. The method of paragraph 41, wherein a ratio of the reagent volume to the feed volume is no larger than 1:10.

43. The method of either one of paragraph 41 or paragraph 42, wherein a ratio of the reagent volume to the feed volume is at least 1:10,000.

44. The method of any one of paragraphs 41-43, wherein the determining a degree of removal of fluorescent viral particles comprises determining a calculated feed concentration of the fluorescent viral particles in the evaluation solution from the analytically quantified number concentration of the viral standard solution used to make the evaluation solution.

45. The method of any one of paragraphs 41-44, wherein the viral standard solution is provided in a sealed container and the method comprises, prior to the combining, unsealing the container and removing from the container the reagent volume of the viral standard solution.

46. The method of paragraph 45, wherein the sealed container comprises viral standard indicia including identity of the viral particles and the analytically quantified number concentration, the viral standard indicia preferably being exteriorly observable.

47. A viral standard product, comprising:
a viral standard solution comprising an analytically quantified number concentration of fluorescent viral particles dispersed in a standard liquid medium, the fluorescent viral particles comprising viral particles and a fluorescent dye conjugated to the viral particles; and
a container, preferably a sealed container, containing the viral standard solution, the container comprising viral standard indicia, the viral standard indicia including identity of the viral particles and the analytically quantified number concentration, the viral standard indicia preferably being exteriorly observable.

48. A method for making a viral standard product, comprising:
harvesting viral particles from a viral particle production operation, as harvested the viral particles being in a harvest solution comprising biological contaminants;

following the harvesting, purification processing of the viral particles to prepare a purified process solution containing the viral particles;

fluorescent labeling the viral particles in the purified process solution to prepare a labeled process solution comprising fluorescent viral particles, the fluorescent labeling comprising conjugating a fluorescent dye to the viral particles; and after the fluorescent labeling, preparing a batch of viral standard solution comprising a batch of the fluorescent viral particles dispersed in a standard liquid medium;

analytically quantifying a number concentration of the fluorescent viral particles in the batch of the viral standard solution; and disposing a volume of the batch of the viral standard solution in a container, preferably a sealed container, wherein the container comprises thereon viral standard indicia including identity of the viral particles and the analytically quantified number concentration, the viral standard indicia preferably being exteriorly observable.

49. The method of paragraph 48, wherein the purification processing comprises a member selected from the group consisting of filtration, chromatography, centrifugation (optionally, ultracentrifugation), membrane separation (optionally dialysis), precipitation (preferably including precipitation of the viral particles) and combinations thereof.

50. The method of either one of paragraph 48 or paragraph 49, wherein the purification processing comprises affinity separation wherein the viral particles adhere to affinity media, and preferably an affinity membrane, and optionally the affinity separation comprises affinity chromatography.

51. The method of any one of paragraphs 48-50, comprising after the fluorescent labeling, second purification processing of the labeled process solution, wherein the batch of the viral standard solution has a higher purity level than the labeled process solution.

52. The method of paragraph 51, wherein the second purification processing comprises at least one member selected from the group consisting of filtration, chromatography, centrifugation and membrane separation.

53. The method of either one of paragraph 51 or paragraph 52, wherein the second purification processing comprises affinity separation wherein the fluorescent viral particles adhere to affinity media, and preferably an affinity membrane, and optionally the second purification processing comprises affinity chromatography.

54. The method of any one of paragraphs 48-53, wherein the viral standard solution comprises a concentration of the fluorescent viral particles of at least an order of magnitude larger than a concentration of the viral particles in the harvest solution, and preferably at least two orders of magnitude larger than a concentration of the viral particles in the harvest solution.

55. The method of any one of paragraphs 48-54, wherein the analytically quantifying comprises flow cytometry evaluation of a sample volume of the viral standard solution, and optionally the flow cytometry evaluation includes subjecting to flow cytometry a dilution series of diluted samples prepared from the sample of the viral standard solution, the dilution series including a plurality of diluted samples prepared at different dilution ratios (preferably at least 3 different dilution ratios).

56. The method of any one of paragraphs 48-54, wherein the analytically quantifying comprises an analytical technique selected from the group consisting of nanoparticle tracking analysis, imaging and microscopy, and preferably nanoparticle tracking analysis.

57. The method of any one of paragraphs 48-56, wherein the fluorescent labeling comprises reacting a reactant molecule comprising the fluorescent dye with a reactive group on a viral protein of the viral particles.

58. The method of paragraph 57, wherein the reactive group is a primary amine.

59. The method of paragraph 58, wherein the primary amine is on lysine amino acid residue in the viral protein.

60. The method of any one of paragraphs 57-59, wherein the reactant molecule comprises a succinimidyl ester.

61. The method of paragraph 60, wherein the reactant molecule comprises a N-hydroxysuccinimide ester.

62. The method of either one of any one of paragraphs 57-59, wherein the reactant molecule comprises a member selected from the group consisting of an isothiocyanate, and isocyanate, a sulfonyl chloride, an aldehyde, a carbodiimide, an acyl azide, an anhydride, a fluorobenzene, a carbonate, an imidoester, an epoxide and a fluorophenyl ester.

63. The method of any one of paragraphs 48-63, wherein the viral standard indicia comprises a member selected from the group consisting of identification of the batch of the source of the volume of the viral standard solution in the container, quantification technique used to determine the analytically quantified number concentration, analytical instrument used (e.g., analytical instrument equipment model) to determine the analytically quantified number concentration and combinations thereof.

64. The method of any one of paragraphs 48-63, comprising preparing from the batch a plurality of aliquots of the viral standard solution each having the volume, and disposing each said aliquot in a different said container, each of which is preferably a sealed container.

65. A kit for viral clearance evaluation for a biological medical product preparation process, the kit comprising:
a viral standard product, the viral standard product comprising a container, preferably a sealed container, containing a viral standard solution for use to prepare evaluation solutions comprising a biological medical product for viral clearance evaluation; and
at least one virus removal device for testing removal of the fluorescent viral particles during purification processing of a said evaluation solution to prepare a treated solution for the viral clearance evaluation; and
wherein, the viral standard solution comprises an analytically quantified number concentration of fluorescent viral particles dispersed in a standard liquid medium, the fluorescent viral particles comprising viral particles and a fluorescent dye conjugated to the viral particles.

66. The kit of paragraph 65, comprising a plurality of different said viral removal devices each comprising a different virus removal technique.

67. The kit of either one of paragraph 65 or paragraph 66, wherein the container is a first container and the kit comprises a second container, which is preferably a sealed container, containing an aqueous sample preparation liquid for use as a predominant component to combine with a quantity of the biological medical product and a quantity of the viral standard product in preparation of a said evaluation solution for viral clearance testing.

68. The kit of paragraph 67, wherein the aqueous sample preparation liquid comprises an aqueous buffered solution.

69. The kit of either one of paragraph 67 or paragraph 68, comprising a volume ratio of the aqueous sample preparation liquid to the viral standard product of at least 5:1, and preferably at least 10:1, and optionally with the volume ratio being no larger than 1000:1.

70. The kit of any one of paragraphs 65-69, comprising a flow cytometer for quantifying a number concentration of the fluorescent viral particles in a liquid solution of the virus clearance evaluation selected from the group consisting of a said evaluation solution, a said treated solution and combinations thereof.

71. The kit of any one of paragraphs 65-70, wherein each said virus removal device is selected from the group consisting of a filter, a chromatographic separator and a membrane separator.

72. The kit of any one of paragraphs 65-71, wherein the container comprises viral standard indicia including identity of the viral particles and the analytically quantified number concentration, the viral standard indicia preferably being exteriorly observable.

73. The kit of any one of paragraphs 46, 47, 48-64 and 72, wherein the viral standard indicia comprise a batch identifier identifying a batch of the viral standards solution contained in the container.

74. The method, product or kit of any one of paragraphs 41-73, wherein the analytically quantified concentration is at least $1 \times 10^7$ particles per milliliter, preferably at least $1 \times 10^8$, more preferably at least $1 \times 10^9$ particles per milliliter, and even more preferably at least $1 \times 10^{10}$ particles per milliliter.

75. The method, product or kit of any one of paragraphs 41-74, wherein the analytically quantified concentration is up to $1 \times 10^{13}$ particles per milliliter.

76. The method, product or kit of any one of paragraphs 41-75, wherein the viral standard solution comprises no greater than 5% of total protein concentration per milliliter of biological proteinaceous contaminants.

77. The method, product or kit of any one of paragraphs 41-76, wherein the viral standard solution comprises a member selected from the group consisting of fetal bovine serum, bovine serum albumin, glycerol, phosphate buffer, other non-phosphate buffer, sucrose, lactose, cyclodextrin, mannitol, trehalose, tertiary amine beta cyclodextrin (TMBCD), poloxamer (e.g., Kolliphor®, Lutrol® or Pluronic® products, with one preferred poloxamer being Poloxamer 188 such as in Kolliphor® P 188 or Lutrol® F 68), DMSO, EDTA, $MgCl_2$ and combinations thereof.

78. The method, product or kit of any one of paragraphs 41-77, wherein the viral standard solution is substantially free of unbound fluorescent dye, preferably having a concentration of unbound fluorescent dye in the viral standard solution of no larger than 1.0 microgram per milliliter, more preferably no larger than 0.1 microgram per milliliter, and even more preferably no larger than 0.01 microgram per milliliter.

79. The method, product or kit of any one of paragraphs 1-78 wherein the viral particles comprise a viral assembly selected from the group consisting of a viral capsid, a viral envelope and combinations thereof.

80. The method, product or kit of any one of paragraphs 1-79, wherein the viral particles are non-infectious and non-replicating.

81. The method, product or kit of any one of paragraphs 1-80, wherein the viral particles are virus-like particles.

82. A method, product or kit of any one of paragraphs 1-81, wherein the viral particles are virions.

83. The method, product or kit of any one of paragraphs 1-82, wherein the viral particles comprise a viral epitope.

84. The method, product or kit of paragraph 83, wherein the viral epitope is of a virus family selected from the group consisting of Parvoviridae, Adenoviridae, Retroviridae, Reoviridae and Herpesviridae.

85. The method, product or kit of any one of paragraphs 1-84, wherein the fluorescent viral particles are of a size with a maximum cross-dimension of no larger than 300 nanometers, often no larger than 200 nanometers and also often no more than 100 nanometers.

86. The method, product or kit of any one of paragraphs 1-85, wherein the fluorescent viral particles are of a size with a maximum cross-dimension of at least 20 nanometers, often at least 25 nanometers, and also often at least 30 nanometers.

87. The method of any one of paragraphs 1-86, wherein the fluorescent viral particles are of a size with a maximum cross-dimension of no more than 4 nanometers larger than, preferably no more 3 nanometers larger than or even no more than 2 nanometers larger than, an original maximum cross-dimension of the viral particles; and often the maximum cross-dimension of the fluorescent particles is at least 1 nanometer larger than an original maximum cross-dimension of the viral particles.

88. The method of any one of paragraphs 1-87, wherein the fluorescent viral particles are in the absence of a fluorescent antibody stain attached to the viral particles.

89. The method of any one of paragraphs 1-88, wherein the fluorescent viral particles comprise the fluorescent dye conjugated to the viral particles through a linkages selected from the group consisting of amide linkages, amidine linkages and combinations thereof.

90. The method of any one of paragraphs 1-89, wherein the fluorescent dye is conjugated to viral protein of the viral particles.

91. The method of paragraph 90, wherein the fluorescent dye is in a moiety including a residual nitrogen of a reacted primary amine of the viral protein, and wherein the moiety has a molecular mass of no larger than 2,500 Daltons, often no larger than 2000 Daltons and also often no larger than 1800 Daltons; and often the moiety has a molecular mass of at least 225 Daltons.

92. The method of either one of paragraph 90 or paragraph 91, wherein the viral protein comprises a viral capsid protein.

93. The method of either one of paragraph 90 or paragraph 91, wherein the viral protein comprises a viral envelope protein.

94. The method of any one of paragraphs 91-93, wherein the primary amine comprises primary amine on lysine amino acid residue.

The terms "comprising", "containing", "including" and "having", and grammatical variations of those terms, are intended to be inclusive and nonlimiting in that the use of such terms indicates the presence of a stated condition or feature, but not to the exclusion of the presence also of any other condition or feature. The use of the terms "comprising", "containing", "including" and "having", and grammatical variations of those terms in referring to the presence of one or more components, subcomponents or materials, also include and is intended to disclose the more specific embodiments in which the term "comprising", "containing", "including" or "having" (or the variation of such term) as the case may be, is replaced by any of the narrower terms "consisting essentially of" or "consisting of" or "consisting of only" (or any appropriate grammatical variation of such narrower terms). For example, a statement that something "comprises" a stated element or elements is also intended to include and disclose the more specific narrower embodiments of the thing "consisting essentially of" the stated element or elements, and the thing "consisting of" the stated element or elements. Examples of various features have been provided for purposes of illustration, and the terms "example", "for example" and the like indicate illustrative examples that are not limiting and are not to be construed or interpreted as limiting a feature or features to any particular example. The term "at least" followed by a number (e.g., "at least one") means that number or more than that number. The term at "at least a portion" means all or a portion that is less than all. The term "at least a part" means all or a part that is less than all. The term "at least a majority" means all or a majority part that is less than all.

What is claimed is:

1. A method for viral clearance evaluation, the method comprising:
    subjecting an evaluation solution to a purification processing to prepare create a treated solution, wherein the evaluation solution comprises fluorescent viral particles, and wherein the purification process comprises at least one viral removal technique for separation of a viral contaminant; and
    determining a degree of removal of the fluorescent viral particles between the evaluation solution and the treated solution;
    wherein the fluorescent viral particles comprise viral particles and a fluorescent dye conjugated to the viral particles;
    wherein the determining a degree of removal of the fluorescent viral particles comprises subjecting a sample of the treated solution to flow cytometry to analytically quantify a residual concentration of the fluorescent viral particles in the treated solution; and
    wherein the flow cytometry comprises detecting for a fluorescent emission signature of the fluorescent dye of the fluorescent viral particles; and
    after the purification process no additional fluorescent stain is added to the treated solution prior to the flow cytometry.

2. The method of claim 1, wherein the at least one removal technique comprises chromatography, filtration, centrifugation, membrane separation, dialysis, or combinations thereof.

3. The method of claim 2, further comprising:
    subjecting each of a plurality of said evaluation solutions, each comprising the fluorescent viral particles, to a different said purification process to create different said treated solutions, wherein each different said purification process includes a different said viral removal technique; and
    determining a said degree of removal of the fluorescent viral particles between each said corresponding pair of a said evaluation solution and a said treated solution for each different said purification process.

4. The method of claim 3, wherein at least two of the different said evaluation solutions have the same composition for evaluation of viral clearance alternatives for the different said evaluation solutions having the same composition.

5. The method of claim 3, wherein at least two of the different said evaluation solutions have different compositions for evaluation of viral clearance.

6. The method of claim 1, wherein:
    the fluorescent viral particles are first said fluorescent viral particles comprising first said viral particles and first said fluorescent dye;
    the evaluation solution comprises second said fluorescent viral particles comprising second said viral particles and second said fluorescent dye;
    the first said viral particles have a first viral epitope of a first virus and the second said viral particles have a second viral epitope of a second virus different than the first virus;
    the first fluorescent dye has a first fluorescent emission signature and the second fluorescent dye has a second fluorescent emission signature, different than the first fluorescent emission signature; and
    the method comprises second determining a degree of removal of the second said fluorescent viral particles between the evaluation solution and the treated solution.

7. The method of claim 1, wherein:
    the evaluation solution is a first said evaluation solution, and the fluorescent viral particles are first said fluorescent viral particles comprising first said viral particles and first said fluorescent dye, the treated solution is a first said treated solution and the determining a degree of removal is a first said determining a degree of removal; and
    the method further comprises:
    subjecting a second said evaluation solution to the purification process to create a second said treated solution, wherein the second said evaluation solution comprises second said fluorescent particles comprising second said viral particles, different than the first said viral particles, and second said fluorescent dye, which second said fluorescent dye may be the same or different than the first said fluorescent dye, and wherein the first fluorescent dye has a first fluorescent emission signature and the second fluorescent dye has a second fluorescent emission signature, which said second fluorescent emission signature may be the same or different than the first fluorescent emission signature; and
    second said determining a degree of removal of the second said fluorescent viral particles between the second said evaluation solution and the second said treated solution.

8. The method claim 1, wherein the evaluation solution comprises biological contaminants, other than the fluorescent viral particles.

9. The method of claim 1, wherein the determining a degree of removal of the fluorescent viral particles comprises:
    determining a feed concentration of the fluorescent viral particles in the evaluation solution.

10. A method for viral clearance evaluation of a biological medical product preparation process, the method comprising:
    subjecting an evaluation solution to a purification process to create a treated solution, wherein the evaluation solution comprises a biological medical product and fluorescent viral particles, and wherein the purification processing comprises a viral removal technique for separation of a viral contaminant from the biological medical product; and
    determining a degree of removal of the fluorescent viral particles between the evaluation solution and the treated solution;
    wherein the fluorescent viral particles comprise viral particles and a fluorescent dye conjugated to the viral particles;
    wherein the determining a degree of removal of the fluorescent viral particles comprises determining a feed concentration of the fluorescent viral particles in the evaluation solution and a residual concentration of the fluorescent viral particles in the treated solution;

wherein the determining the residual concentration comprises subjecting a sample of the treated solution to flow cytometry to analytically quantify the residual concentration of the fluorescent viral particles in the evaluation solution; and wherein the flow cytometry comprises detecting for a fluorescent emission signature of the fluorescent dye of the fluorescent viral particles; and after the purification process no additional fluorescent stain is added to the treated solution prior to the flow cytometry.

11. The method of claim 9, wherein the determining a degree of removal of the fluorescent viral particles comprises subjecting a sample volume of the evaluation solution to flow cytometry to analytically quantify a feed concentration of the fluorescent viral particles in the evaluation solution from the fluorescent properties of the fluorescent viral particles.

12. The method of claim 1, comprising preparing the evaluation solution, wherein the preparing the evaluation solution comprises:

combining a feed volume of a preliminary feed solution with a reagent volume of a viral standard solution comprising the fluorescent viral particles dispersed in a standard liquid medium at an analytically quantified number concentration.

13. The method of claim 12, wherein the determining a degree of removal of fluorescent viral particles comprises calculating a feed concentration ($C_F$) of the fluorescent viral particles in the evaluation solution by the following calculation:

$$C_F = C_{AQ} \times V_R / (V_F + V_R)$$

where $V_F$ is the feed volume of the preliminary feed solution, $V_R$ is the reagent volume of the viral standard solution combined to make the evaluation solution, and $C_{AQ}$ is the analytically quantified number concentration of the viral standard solution.

14. The method of claim 1, wherein the viral particles are non-infectious and non-replicating.

15. The method of claim 1, wherein the viral particles comprise a viral epitope of a virus family selected from the group consisting of Parvoviridae, Adenoviridae, Retroviridae, Reoviridae and Herpesviridae.

16. The method of claim 1, wherein the fluorescent viral particles are of a size with a maximum cross-dimension of no more than 4 nanometers larger than an original maximum cross-dimension of the viral particles.

17. The method of claim 16, wherein:

the fluorescent dye is conjugated to a viral protein of the viral particles and the fluorescent dye is in a moiety including a residual nitrogen of a reacted primary amine of the viral protein, and wherein the moiety has a molecular mass of no larger than 2,500 Daltons.

18. The method of claim 1, wherein the evaluation solution further comprises a biological medical product.

19. The method of claim 18, wherein the biological medical product is derived from a cell culture of a characterized cell line.

20. The method of claim 18, wherein the evaluation solution comprises biological contaminants, other than the fluorescent viral particles, representative of a biological medical product preparation process to make the biological medical product.

21. A method for viral clearance evaluation for a biological medical product preparation process, the method comprising:

subjecting an evaluation solution to a purification process to create a treated solution, wherein the evaluation solution comprises a biological medical product and fluorescent viral particles, and wherein the purification process comprises a viral removal technique for separation of a viral contaminant from the biological medical product; and determining a degree of removal of the fluorescent viral particles between the evaluation solution and the treated solution;

wherein the fluorescent viral particles comprise viral particles and a fluorescent dye conjugated to the viral particles;

wherein the determining a degree of removal of the fluorescent viral particles comprises subjecting a sample of the treated solution to flow cytometry to analytically quantify a residual concentration of the fluorescent viral particles in the treated solution; and wherein the flow cytometry comprising detecting for a fluorescent emission signature of the fluorescent dye of the fluorescent viral particles; and after the purification process no additional fluorescent stain is added to the treated solution prior to the flow cytometry.

22. The method of claim 21, wherein the determining a degree of removal of the fluorescent viral particles comprises subjecting a sample volume of the evaluation solution to an analytical technique to analytically quantify a feed concentration of the fluorescent viral particles in the evaluation solution from the fluorescent properties of the fluorescent viral particles.

23. The method of claim 1, wherein after the purification process there is no chemical modification of the treated solution prior to the flow cytometry.

* * * * *